(12) United States Patent
Martemyanov et al.

(10) Patent No.: US 12,042,496 B2
(45) Date of Patent: Jul. 23, 2024

(54) METHODS RELATED TO OPIOID THERAPEUTICS

(71) Applicant: University of FLorida Research Foundation, Incorporated, Gainesville, FL (US)

(72) Inventors: Kirill Martemyanov, Jupiter, FL (US); Brock Grill, Lake Worth, FL (US)

(73) Assignee: THE UNIVERSITY OF FLORIDA RESEARCH FOUNDATION, INCORPORATED, Gainesville, FL (US)

( * ) Notice: Subject to any disclaimer, the term of this patent is extended or adjusted under 35 U.S.C. 154(b) by 396 days.

(21) Appl. No.: 17/286,187

(22) PCT Filed: Oct. 15, 2019

(86) PCT No.: PCT/US2019/056284
§ 371 (c)(1),
(2) Date: Apr. 16, 2021

(87) PCT Pub. No.: WO2020/081538
PCT Pub. Date: Apr. 23, 2020

(65) Prior Publication Data
US 2021/0338680 A1 Nov. 4, 2021

Related U.S. Application Data

(60) Provisional application No. 62/746,343, filed on Oct. 16, 2018.

(51) Int. Cl.
| | |
|---|---|
| *A61K 31/519* | (2006.01) |
| *A61K 31/095* | (2006.01) |
| *A61K 31/166* | (2006.01) |
| *A61K 31/175* | (2006.01) |
| *A61K 31/397* | (2006.01) |
| *A61P 25/36* | (2006.01) |

(52) U.S. Cl.
CPC .......... *A61K 31/519* (2013.01); *A61K 31/095* (2013.01); *A61K 31/166* (2013.01); *A61K 31/175* (2013.01); *A61K 31/397* (2013.01); *A61P 25/36* (2018.01)

(58) Field of Classification Search
CPC .............................. A61K 31/519; A61P 25/36
IPC ...................................................... A61K 31/519
See application file for complete search history.

(56) References Cited

U.S. PATENT DOCUMENTS

| | | |
|---|---|---|
| 2016/0022636 A1 | 1/2016 | Dvorak et al. |
| 2017/0095480 A1 | 4/2017 | Hitchcock et al. |
| 2017/0348319 A1* | 12/2017 | Hitchcock ............... A61P 25/28 |

FOREIGN PATENT DOCUMENTS

| | | |
|---|---|---|
| WO | WO-2014/152917 A2 | 9/2014 |
| WO | WO-2020081538 A1 | 4/2020 |

OTHER PUBLICATIONS

Kononoff et al., Systemic and Intra-Habenular Activation of the Orphan G Protein-Coupled Receptor GPR139 Decreases Compulsive-Like Alcohol Drinking and Hyperalgesia in Alcohol-Dependent Rats, eNeuro, Jul. 2, 2018;5(3).*
Wang et al., High-throughput screening of antagonists for the orphan G-protein coupled receptor GPR139, Acta Pharmacol Sin. Jul. 2015;36(7):874-8.*
Carney, Identification of a Novel Molecular Target for Alcohol Dependence, eNeuro, Jul./Aug. 2018, 5(4) e0255-18.2018 1-3.*
Hashimoto et al., Enhancement of Morphine Analgesic Effect with Induction of μ-Opioid Receptor Endocytosis in Rats, Anesthesiology, Sep. 2006, vol. 105, 574-580.*
"International Application Serial No. PCT/US2019/056284, International Search Report mailed Jan. 30, 2020", 2 pgs.
"International Application Serial No. PCT/US2019/056284, Written Opinion mailed Jan. 30, 2020", 4 pgs.
Hashimoto, Tatsuya, et al., "Enhancement of Morphine Analgesic Effect with Induction of μ-Opioid Receptor Endocytosis in Rats", Anesthesiology, (2006), 574-80.
Wang, Jia, et al., "High-throughput screening of antagonists for the orphan G-protein coupled receptor GPR139", Acta Pharmacol Sin, (2015), 874-8.
"International Application Serial No. PCT US2019 056284, International Preliminary Report on Patentability mailed Apr. 29, 2021", 6 pgs.
Dvorak, Curt A., "Identification and SAR of Glycine Benzamides as Potent Agonists for the GPR139 Receptor", ACS Med. Chem. Lett. 6(9) (2015) 1015-1018, (Jul. 20, 2015), 1015-1018.
Hu, Liaoyuan A., "Identification of Surrogate Agonists and Antagonists for Orphan G-Protein-Coupled Receptor GPR139", 2009 Society for Biomolecular Sciences, (2009), 9 pages.
Liu, Changlu, "GPR139, an Orphan Receptor Highly Enriched in the Habenula and Septum, Is Activated by the Essential Amino Acids L-Tryptophan and L-Phenylalanine", 2015 by The American Society for Pharmacology and Experimental Therapeutics, (Nov. 2015), 15 pages.
Nohr, Anne Cathrine, "The orphan G protein-coupled receptor GPR139 is activated by the peptides: Adrenocorticotropic hormone (ACTH), a-, and b-melanocyte stimulating hormone (a-MSH, and b-MSH), and the conserved core motif HFRW", Neurochemistry International 102 (2017), (2017), 9 pages.

(Continued)

Primary Examiner — Svetlana M Ivanova
(74) Attorney, Agent, or Firm — Alston & Bird LLP

(57) ABSTRACT

The present invention provides methods for modulating opioid receptor mediated analgesic effect, e.g., promoting or enhancing analgesia in subjects in need of pain relief. Also provided in the invention are methods for ameliorating or suppressing withdrawal symptoms in subjects with chronic opioid use. These methods of the invention entail administering to the subjects in need of treatment a therapeutically effective amount of a GPR139 antagonist compound. The invention further provides methods for identifying novel compounds that can be useful for modulating opioid receptor mediated analgesic effect.

7 Claims, 14 Drawing Sheets

(56) References Cited

OTHER PUBLICATIONS

Shi, Feng, "Discovery and SAR of a Series of Agonists at Orphan G Protein-Coupled Receptor 139", ACS Med. Chem. Lett. 2(4) (2011) 303-306, (Feb. 28, 2011), 303-306.

* cited by examiner

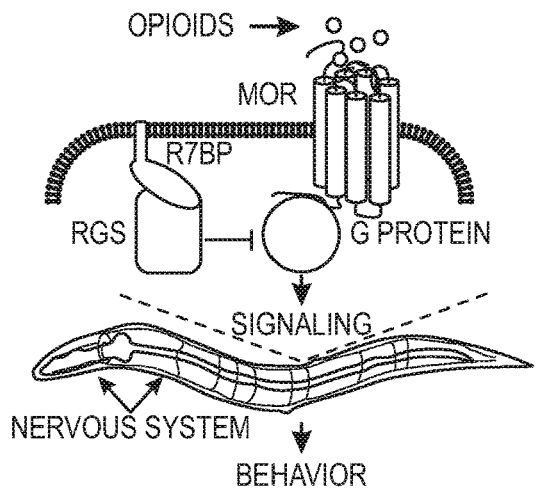
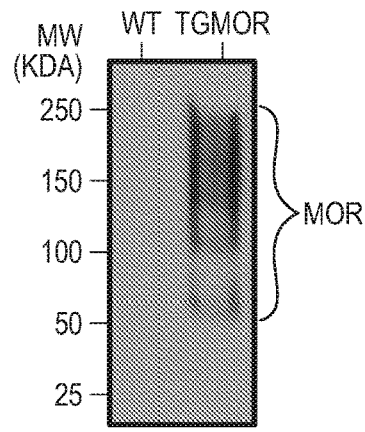
FIG. 1A
FIG. 1B
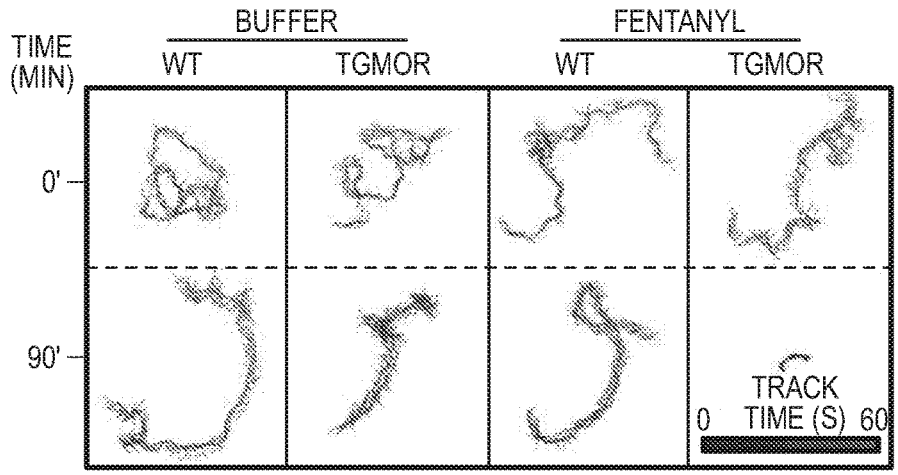
FIG. 1C
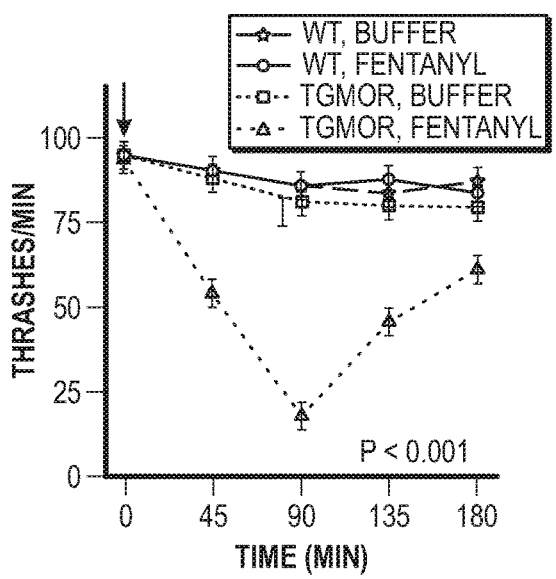
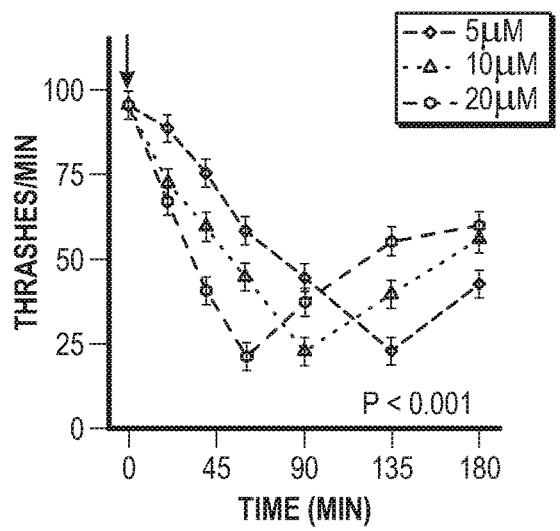
FIG. 1D
FIG. 1E

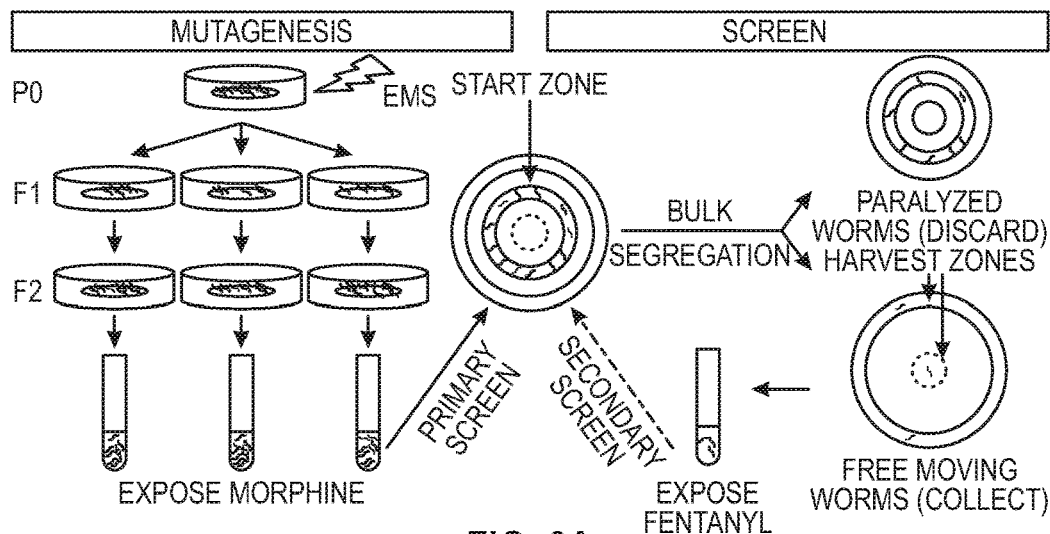
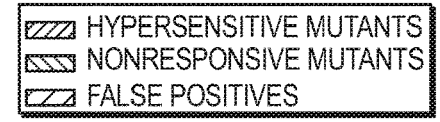
FIG. 2A
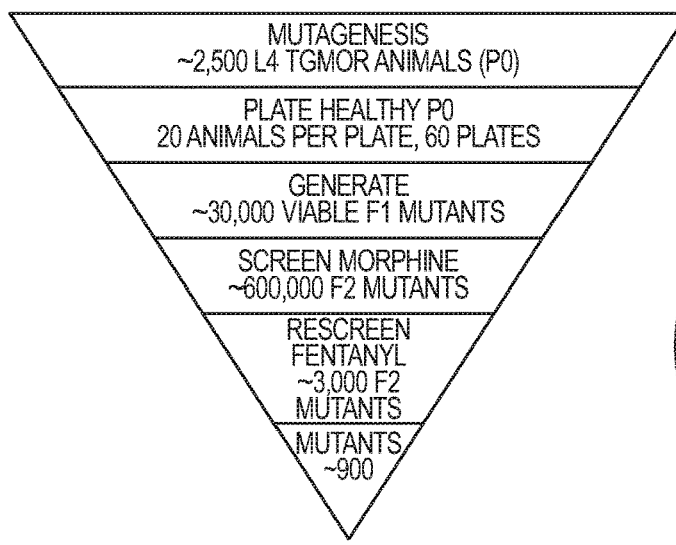
FIG. 2B
FIG. 2C
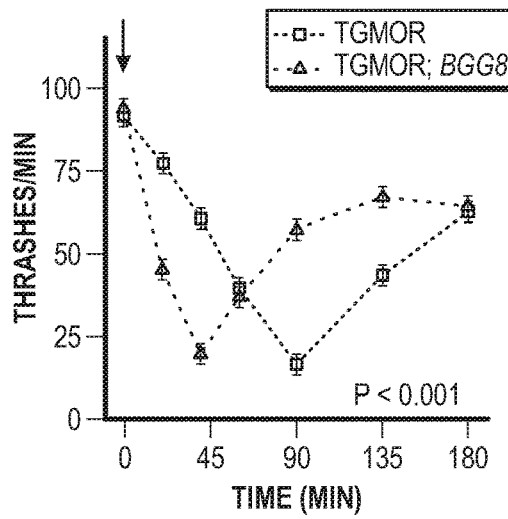
FIG. 2D
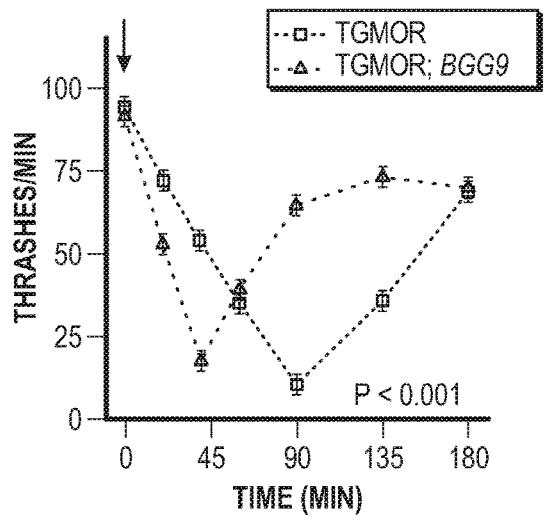
FIG. 2E

METHODS RELATED TO OPIOID THERAPEUTICS

PRIORITY CLAIM TO RELATED APPLICATIONS

This application is a U.S. national stage filing under 35 U.S.C. § 371 from International Application No. PCT/US2019/056284, filed on 15 Oct. 2019, and published as WO2020/081538 on 23 Apr. 2020, which claims the benefit under 35 U.S.C. 119(e) to U.S. Provisional Application No. 62/746,343, filed on 16 Oct. 2018, the benefit of priority of each of which is claimed herein, and which applications and publication are hereby incorporated herein by reference in their entirety.

CLAIM OF PRIORITY

This application claims the benefit of priority to U.S. Provisional Application Ser. No. 62/746,343, filed on Oct. 16, 2018, which is incorporated herein by reference in its entirety.

STATEMENT OF GOVERNMENT SUPPORT

This invention was made with government support under grant numbers DA040406 and DA036596 awarded by the National Institutes of Health. The government has certain rights in the invention.

BACKGROUND OF THE INVENTION

G protein coupled receptors (GPCRs) constitute the largest class of cell surface receptors and are responsible for sensory perception and cellular communication via hormones and neurotransmitters. GPCRs are also heavily involved in disease and are the most prominent drug targets. Insufficient understanding of GPCR signaling significantly hampers their targeting by drugs in a safe and effective manner. This is well illustrated by opioid analgesics that act on the µ-opioid receptor (MOR): they offer unsurpassed efficacy for pain management. However, virtually all FDA approved opioid drugs come with substantial liabilities including: dependence, loss of efficacy over time, and somatic side effects. Extensive investigation of MOR pharmacology led to the concept that activated MOR triggers distinct signaling events that can be differentially dissociated to control various physiological reactions. Nonetheless, very little is known about the identity of biasing factors that route MOR signals and determine their efficacy in vivo.

There are unmet needs in the art for means to better understand MOR signaling in endogenous neural circuits, and for novel agents that can increase efficacy and safety of opioid analgesics by modulating MOR signaling in vivo. There is also a need in the art for more effective treatment for opioid dependence and withdrawal. The present invention addresses these and other needs.

SUMMARY OF THE INVENTION

In one aspect, the invention relates to methods for providing or enhancing analgesic effect mediated by the µ-opioid receptor (MOR) in a subject. These methods entail administering to the subject a pharmaceutical composition than contains an effective amount of a compound that down-regulates expression or cellular activity of GPR139 or an ortholog thereof, which leads to stimulation or enhancement of MOR mediated analgesic effect in the subject. In some methods, the administered compound promotes MOR signaling mediated by endogenous ligands in the subject. In some other methods, the subject is administered with an opioid drug for pain relief, and the administered compound enhances the effect of the exogenously administered opioid drug. In these methods, the subject can be administered with the opioid drug prior to, simultaneously with, or subsequent to administration of the pharmaceutical composition. In various embodiments, the opioid drug taken by the subject can be, e.g., oxycodone, hydrocodone, morphine, codeine, fentanyl, buprenorphine or methadone. In some embodiments, the subject is a human patient.

In some embodiments, the administered agent down-regulates GPCR signaling activity of GPR139 or an ortholog thereof. In some of these methods, the agent is a small organic molecule. For example, the administered agent can be a small organic compound selected from the group consisting of NCRW0001-C02, NCRW0005-F05, NCRW0008-C04, NCRW0095-F03, NCRW0105-E06 (J. Wang et al., *Acta Pharmacol. Sin.* 36(7) (2015) 874-878), LP-114958 and LP-471756 (L. A. Hu et al., *J. Biomolec. Screening* 14(7) (2009) 789-797) as summarized in Table 1 below:

TABLE 1

| Compound Identifier | Compound Structure |
| --- | --- |
| NCRW0001-C02 | 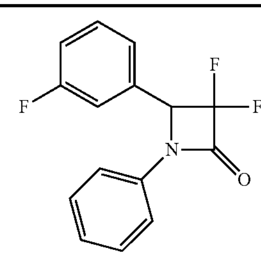 |
| NCRW0005-F05 | 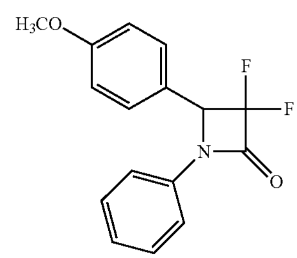 [SMILES: COc1ccc(C2N(c3ccccc3)C(=O)C2(F)F)cc1] |
| NCRW0008-C04 | 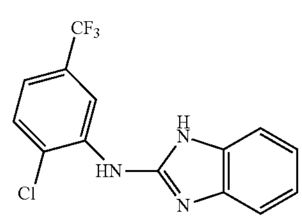 [SMILES: FC(F)(F)c1ccc(Cl)c(Nc2nc3ccccc3[nH]2)c1] |
| NCRW0095-F03 | 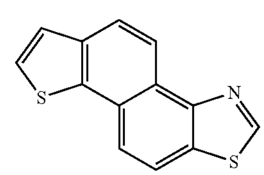 [SMILES: c1nc2c(ccc3c2ccc2ccsc23)s1] |

TABLE 1-continued

| Compound Identifier | Compound Structure |
| --- | --- |
| NCRW0105-E06 | 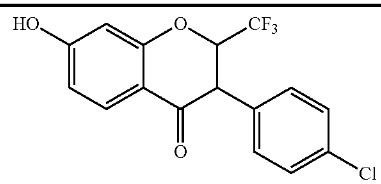 |
| LP-114958 | 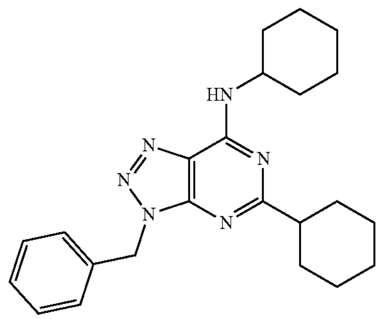 [SMILES: c1ccc(Cn2nnc3c(NC4CCCCC4)nc(C4CCCCC4)nc32)cc1] |
| LP-471756 | 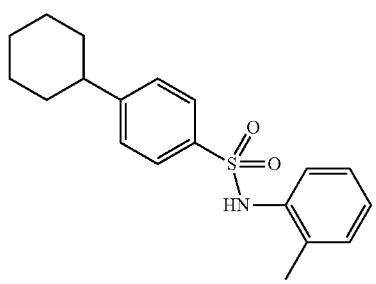 [SMILES: Cc1ccccc1NS(=O)(=O)c1ccc(C2CCCCC2)cc1] |

In some other embodiments, the agent down-regulates cellular level of GPR139 or an ortholog thereof. In some of these methods, the administered agent can be, e.g., a short interfering RNA (siRNA) or an anti-sense nucleic acid that specifically targets GPR139 or an ortholog thereof.

In a related aspect, the invention provides methods for suppressing or ameliorating withdrawal symptoms in subjects with chronic use of an opioid drug. These methods entail administering to the subject a pharmaceutical composition that contains an effective amount of a compound that down-regulates expression or cellular activity of GPR139 or an ortholog thereof, which results in suppressing or ameliorating of withdrawal symptoms in the subject. In some methods, the subject is administered with the pharmaceutical composition after discontinuing use of the opioid dug. In various embodiments, the opioid drug used by the subject is oxycodone, hydrocodone, morphine, codeine or fentanyl. In some embodiments, the subject in need of treatment is human. In some embodiments, the administered GPR139 antagonist down-regulates GPCR signaling activity of GPR139 or an ortholog thereof. In some of these embodiments, the administered GPR139 antagonist is a small organic molecule, e.g., NCRW0001-C02, NCRW0005-F05, NCRW0008-C04, NCRW0095-F03, NCRW0105-E06, LP-114958 and LP-471756. In some other embodiments, the administered GPR139 antagonist down-regulates cellular level of GPR139 or an ortholog thereof. For example, the GPR139 antagonist employed in the methods can be a short interfering RNA (siRNA) or an anti-sense nucleic acid that specifically targets GPR139 or an ortholog thereof.

In another aspect, the invention provides methods for reducing reward or diminishing reinforcing effects of opioid drugs for treating or preventing addiction in a subject. These methods involve administering to the subject a pharmaceutical composition than contains an effective amount of a compound that up-regulates expression or cellular activity of GPR139 or an ortholog thereof. In various embodiments, the GRP139 agonist compound administered to the subject can be any agent described herein, e.g., 2-(3,5-dimethoxybenzoyl)-N-(naphthalen-1-yl)hydrazine-1-carboxamide (F. Shi et al. *ACS Med. Chem. Lett.* 2(4) (2011) 303-306), JNJ-63533054 and [$^3$H]JNJ-63533054 (Liu et al., *Mol. Pharmacol.* 2015; 88:911-925); TAK-041, 923580, 923581, 923582, and 923582 (US 2017/0095480); and other glycine benzamides as described in C. Dvorak et al., *ACS Med. Chem. Lett.* 6(9) (2015) 1015-1018 (Table 2).

TABLE 2

| Compound Identifier | Compound Structure |
| --- | --- |
| 2-(3,5-dimethoxybenzoyl)-N-(naphthalen-1-yl)hydrazine-1-carboxamide | |
| JNJ-63533054 | 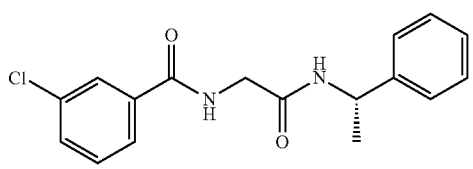 [SMILES: C[C@H](NC(=O)CNC(=O)c1cccc(Cl)c1)c1ccccc1] |

TABLE 2-continued

| Compound Identifier | Compound Structure |
| --- | --- |
| [³H]JNJ-63533054 | |
| 3-Methoxy-N-(2-oxo-2-[[(1S)-1-phenylethyl]amino]ethyl)benzamide | 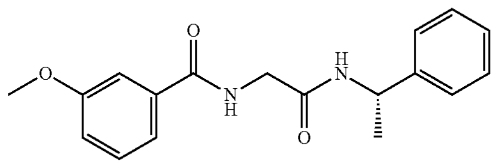 [SMILES: COc1cccc(C(=O)NCC(=O)N[C@@H](C)c2ccccc2)c1] |
| TAK-041 | 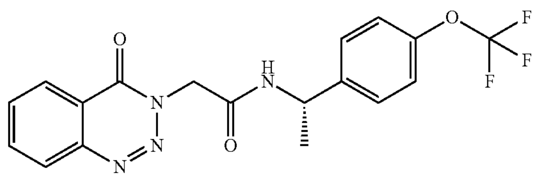 [SMILES: C[C@H](NC(=O)Cn1nnc2ccccc2c1=O)c1ccc(OC(F)(F)F)cc1] |
| 923580 | 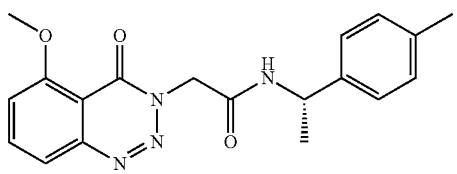 [SMILES: COc1cccc2nnn(CC(=O)N[C@@H](C)c3ccc(C)cc3)c(=O)c12] |
| 923581 | 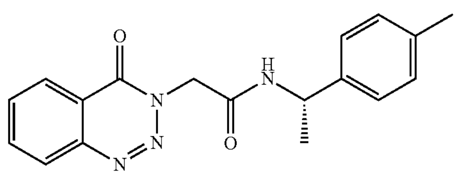 [SMILES: Cc1ccc([C@H](C)NC(=O)Cn2nnc3ccccc3c2=O)cc1] |
| 923582 | 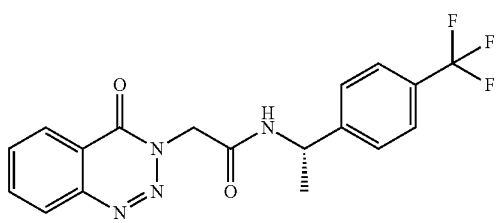 [SMILES: C[C@H](NC(=O)Cn1nnc2ccccc2c1=O)c1ccc(C(F)(F)F)cc1] |
| 923583 | 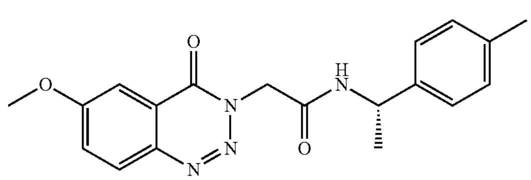 |
| 2-(3,5-dimethoxybenzoyl)-N-(naphthalen-1-yl)hydrazine-1-carboxamide | |

In still another aspect, the invention provides methods for identifying an agent that modulates the μ-opioid receptor (MOR) signaling. These methods involve (a) screening test compounds to identify one or more modulating compounds that modulate expression or cellular activity of GPR139 or an ortholog thereof, and (b) testing the modulating compounds and selecting one or more of the compounds that are able to modulate an MOR signaling related activity, thereby allowing identification of agents that modulate MOR signaling. In some of these screening methods, the modulating compounds are identified from Step (a) for ability to down-regulate expression or cellular level of GPR139 or an ortholog thereof. In some other methods, the candidate or test compounds are screened in Step (a) for ability to up-regulate expression or cellular level of GPR139 or an ortholog thereof. In some other embodiments, the candidate or test compounds are screened in Step (a) for ability to down-regulate a GPCR signaling function of GPR139. In still some other embodiments, the candidate or test compounds are screened in Step (a) for ability to up-regulate a GPCR signaling function of GPR139.

In some screening methods, Step (b) entails testing the modulating compounds identified from Step (a) for ability to modulate MOR mediated activation of G protein gated inwardly rectifying $K^+$ (GIRK) channels. In some other methods, Step (b) entails testing the modulating compounds identified from Step (a) for ability to modulate morphine analgesia, withdrawal or reinforcing effect in a non-human animal. Some of the screening methods are directed to identifying MOR agonists. In these methods, the modulating compounds identified from Step (a) are then examined for ability to increase maximal response to morphine and duration of analgesic effect, diminishes withdrawal symptoms, or reduces reinforcing effect in the non-human animal. Some other screening methods are directed to identifying MOR antagonists. In these methods, the modulating compounds identified from Step (a) are then examined for ability to decrease maximal response to morphine and duration of analgesic effect.

A further understanding of the nature and advantages of the present invention may be realized by reference to the remaining portions of the specification and claims.

BRIEF DESCRIPTION OF THE DRAWINGS

FIG. 2 shows forward genetic screen for modulators of opioid sensitivity in tgMOR platform. (A) Two-step genetic screen for tgMOR mutants with altered opioid sensitivity. (B) Outline of steps, generations and mutant numbers isolated in genetic screen with tgMOR. (C) Distribution of independent isolates from mutant screen across phenotypic categories. (D, E) Time course of fentanyl effects on hypersensitive mutants: tgMOR; bgg8 (D) and tgMOR; bgg9 (E). Arrows denote application of fentanyl (10 μM). Significance tested using two-way ANOVA.

DETAILED DESCRIPTION OF THE INVENTION

Figure 1F:
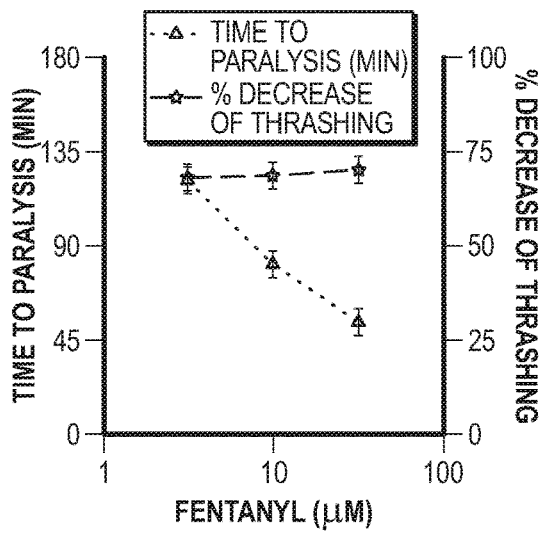
FIG. 1 illustrates transgenic *C. elegans* platform for dissection of opioid signaling mechanisms. (A) Transgenic *C. elegans* model of MOR signaling (tgMOR). (B) Western blot showing expression of FLAG::MOR in the nervous system. (C) Fentanyl inhibits thrashing of tgMOR. (D) Quantitation of fentanyl effects on tgMOR. (E) Time course of fentanyl doses on tgMOR. (F) Fentanyl dose response for tgMOR. (G) Time course for morphine and fentanyl on tgMOR. (H) Morphine and fentanyl dose response for tgMOR. (I) Naloxone blocks fentanyl effects on tgMOR. (J, K) Time courses showing tgMOR; rsbp-1 mutants are hypersensitive to fentanyl (J) and morphine (K). Arrows denote drug application. Significance tested using two-way ANOVA.

Opioid analgesics offer unrivaled pain management but have severe abuse liability. Opioids produce clinically significant effects via the µ-opioid receptor (MOR), a member of the G protein Coupled Receptor (GPCR) family. Saturation of MOR as a drug target presents a pressing need to discover new modifiers that alter MOR signaling outcomes.

The present invention is derived in part from the development by the inventors of a whole animal behavioral platform for unbiased discovery of genes influencing opioid responsiveness. As detailed herein, the inventors utilized forward genetics in transgenic *C. elegans* expressing mammalian MOR and identified a conserved orphan receptor FRPR-13 in *C. elegans* and GPR139 in mammals with anti-opioid activity. Cell-based assays revealed that GPR139 inhibits MOR. GPR139 is coexpressed with MOR in select brain circuits underlying opioid action. Elimination of GPR139 in mice augments morphine-induced analgesia and reward, but diminishes dependence. These data indicate that GPR139 is a novel target for increasing safety of opioid pharmacotherapies, and showcase *C. elegans* as a scalable platform for genetic discovery of novel GPCR signaling principles.

In accordance with the discoveries described herein, the invention provides methods for modulating analgesic response in subjects who are taking opioid related drugs. For example, GPR139 antagonists could increase the efficacy of existing blockbuster opioid drugs, while diminishing their dependence-causing liability. Some embodiments of the invention are directed to use of GPR139 agonists for diminishing reinforcing effects (reward) of opioids in subjects to treat or prevent addiction. Subjects suitable for such a treatment can be one who is either an acute user or a chronic used of opioids. In some related embodiments, the invention also provides clinical methods for providing analgesic response by targeting GPR139 and enhancing endogenous opioid signaling. Further provided in the invention are methods for identifying novel drugs that modulate MOR signaling. Such novel drugs can be identified by testing candidate compounds for ability to modulate GPR139, e.g., antagonizing or agonizing the GPCR signaling function of GPR139. The following disclosures provide more detailed guidance for practicing the invention.

Unless defined otherwise, all technical and scientific terms used herein have the same meaning as commonly understood by those of ordinary skill in the art to which this invention pertains. The following references provide one of skill with a general definition of many of the terms used in this invention: *Academic Press Dictionary of Science and Technology*, Morris (Ed.), Academic Press (1$^{st}$ ed., 1992); *Illustrated Dictionary of Immunology*, Cruse (Ed.), CRC Pr I LIc (2$^{nd}$ ed., 2002); *Oxford Dictionary of Biochemistry and Molecular Biology*, Smith et al. (Eds.), Oxford University Press (revised ed., 2000); *Encyclopaedic Dictionary of Chemistry*, Kumar (Ed.), Anmol Publications Pvt. Ltd. (2002); *Dictionary of Microbiology and Molecular Biology*, Singleton et al. (Eds.), John Wiley & Sons (3$^{rd}$ ed., 2002); *Dictionary of Chemistry*, Hunt (Ed.), Routledge (1$^{st}$ ed., 1999); *Dictionary of Pharmaceutical Medicine*, Nahler (Ed.), Springer-Verlag Telos (1994); *Dictionary of Organic Chemistry*, Kumar and Anandand (Eds.), Anmol Publications Pvt. Ltd. (2002); *A Dictionary of Biology (Oxford Paperback Reference)*, Martin and Hine (Eds.), Oxford University Press (4' ed., 2000); and *Diagnostic and Statistical Manual of Mental Disorders*, American Psychiatric Publishing, Inc., 4$^{th}$ Ed. (1994; "DSM-IV") and (2000; "DSM-IV-TR"). In addition, the following definitions are provided to assist the reader in the practice of the invention.

The term "analog" is used herein to refer to a molecule that structurally resembles a reference molecule (e.g., a GPR139 antagonist) but which has been modified in a targeted and controlled manner, by replacing a specific substituent of the reference molecule with an alternate substituent. Compared to the reference molecule, an analog would be expected, by one skilled in the art, to exhibit the same, similar, or improved utility. Synthesis and screening of analogs, to identify variants of known compounds having improved characteristics (such as higher binding affinity for a target molecule) is an approach that is well known in pharmaceutical chemistry.

GPR139 is an orphan receptor identified from bioinformatics analysis of the human genome. It has been shown to have a high mRNA expression in the brain, particularly in the striatum and hypothalamus. Tryptophan, phenylalanine, and α-MSH derived peptides have been identified as putative endogenous ligands of GPR139. But the main signal transduction pathway of GPR139 has not been established. GPR139 is believed to be involved in movement control and/or the regulation of food intake/metabolism, and could play a role in the control of locomotor activity. GPR139 has been suggested as a potential target for the treatment of Parkinson's disease, obesity, eating disorders, and/or diabetes.

As used herein, the terms opioids, opioid drugs, or opioid related drugs or compounds refer to a class of drugs either derived from, or chemically similar to, compounds found in opium poppies. Examples of opioids include legal prescription painkillers like oxycodone (OxyContin®), hydrocodone (Vicodin®), morphine, codeine, fentanyl, and others. Opioid compounds also include antagonist drugs such as naloxone, and endogenous peptides such as the endorphins. In some embodiments, opioid compounds can also include partial agonists of MOR, e.g. buprenorphine and methadone.

The terms "treatment" or "treating" as used herein refers to partially or completely alleviating, inhibiting, preventing, ameliorating and/or relieving a disease or disorder, or one or more symptoms thereof. Treatment can be therapeutic or prophylactic in nature.

The term "subject" or "patient" refers to a mammal, e.g., human or non-human animals. In particular, the term refers to a male or female human being of any race, national origin, age, physiological make-up, genetic make-up, disease predisposition, height, or weight. Unless otherwise noted, the term subject as used in the present disclosure typically refers to one who is taking an opioid drug for acute pain relief. The term also refers to one who has used or has been using an opioid drug chronically, and has developed or is at risk of developing withdrawal symptoms, relapse and/or stance dependence.

Dependence or dependence syndrome refers to a cluster of behavioral, cognitive, and physiological phenomena that may develop after repeated substance use (e.g., opioid use). Typically, these phenomena include a strong desire to take the drug, impaired control over its use, persistent use despite harmful consequences, a higher priority given to drug use than to other activities and obligations, increased tolerance, and a physical withdrawal reaction when drug use is discontinued. In International Statistical Classification of Diseases and Related Health Problems (ICD-10), the diagnosis of dependence syndrome is made if three or more of six specified criteria were experienced within a year. The dependence syndrome may relate to a specific substance (e.g., morphine), a class of substances (e.g., opioid related drugs), or a wider range of pharmacologically different substances.

The term withdrawal, withdrawal symptoms, or withdrawal syndrome refers to a collection of symptoms of variable clustering and degree of severity which occur on cessation or abrupt reduction of use of a psychoactive substance (e.g., an opioid drug) that has been taken repeatedly, usually for a prolonged period and/or in high doses. The syndrome may be accompanied by signs of physiological disturbance. A withdrawal syndrome is one of the indicators of a dependence syndrome. It is also the defining characteristic of the narrower psycho-pharmacological meaning of dependence. The onset and course of the withdrawal syndrome are time-limited and are related to the type of substance and dose being taken immediately before cessation or reduction of use.

The μ-opioid receptors (MOR) are a class of opioid receptors with a high affinity for endogenous opioid peptides enkephalins and beta-endorphin, but a low affinity for dynorphins. They are also referred to as μ-opioid peptide (MOP) receptors. The prototypical exogenous μ-opioid receptor agonist is morphine, the primary psychoactive alkaloid in opium. It is an inhibitory G-protein coupled receptor that activates several inhibitory G protein subunits including Gi alpha, Go alpha, Gz alpha and G beta gamma, inhibiting activity of adenylate cyclase to lower cAMP levels and several ion channels to reduce neuronal excitability and synaptic transmission. Activation of the μ-opioid receptor by an agonist such as morphine causes analgesia, sedation, slightly reduced blood pressure, itching, nausea, euphoria, decreased respiration, miosis (constricted pupils), and decreased bowel motility often leading to constipation. Some of these effects, such as analgesia, sedation, euphoria, itching and decreased respiration, tend to lessen with continued use as tolerance develops. As with other G protein-coupled receptors, signaling by the μ-opioid receptor is terminated through several different mechanisms, which are upregulated with chronic use, leading to rapid tachyphylaxis.

In one aspect, the invention provides therapeutic methods for modulating cellular activities mediated by the μ-opioid receptor (MOR) signaling. For example, the subjects to be treated with methods of the invention are human patients. In general, the therapeutic methods of the invention employ a compound that is capable of modulating GPR139 expression level or biological functions. As demonstrated herein, down-regulation of GPR139 leads to enhanced MOR signaling and sensitivity to opioid compounds. By contrast, up-regulation of GPR139 results in inhibition of MOR signaling and opioid efficacy. The compounds modulating GPR139 to be used in the methods of the invention can be any agents that can alter expression, cellular level, or biochemical activities of GPR139. These include any known compounds that antagonize or agonize the G protein coupled receptor function of GPR139, and inhibitory nucleic acid agents that are specific for polynucleotide sequences encoding GPR139. They also include additional agents, e.g., small molecule compounds or antibodies targeting GPR139, that can be identified or generated in accordance with methods exemplified herein or standard screening methods routinely practiced in the art.

In some preferred embodiments, subjects in need of treatment are administered a GPR139 antagonist described herein to promote MOR mediated signaling activities. As demonstrated herein, down-regulation of GPR139 can lead to enhanced opioid efficacy, e.g., increased sensitivity to the acute effects of morphine. In addition, targeting GPR139 also benefits subjects who have taken morphine chronically by diminishing dependence and ameliorating withdrawal symptoms. Some methods of the invention are directed to reinforcing opioid mediated analgesic effects in subjects who are currently taking opioid related dugs for pain relief. Some methods are directed to providing analgesic relief to subjects not taking opioid drugs by enhancing endogenous MOR signaling for pain relief. In these methods, the subjects can be administered with a pharmaceutical composition containing a therapeutically effective amount of a GPR139 antagonist described herein. To reinforce opioid analgesic effects in subjects who are taking an opioid drug, the GPR139 antagonist can be administered to the subjects prior to, simultaneously with, or subsequent to administration of the opioid drug.

Some other methods are directed to reducing dependence, controlling relapse, suppressing or ameliorating withdrawal symptoms in subjects who have been chronically taking opioid related drugs. In these methods, the GRP139 antagonist can be administered to the subjects after or before they have terminated use of opioid drugs. In some embodiments, the GPR139 antagonist compounds can be administered to the subjects who have discontinued opioid administration and have shown dependence or withdrawal symptoms. In various embodiments, subjects to be treated with these methods typically have ceased or substantially reduced opioid consumption for at least about 1-5 days, e.g., at least 1 day, at least 2 days, at least 3 days, at least 4 days or at least 5 days. Some other methods are directed to treating subjects who have ceased or substantially reduced opioid consumption for a period that is at least 7 days, 2 weeks, 1 month, 3 months, 6 months, 1 year, 2 years or longer.

Subjects taking any opioid related drugs are amenable to treatment with methods of the invention. These include, e.g., morphine and synthetic opioid related compounds such as methadone, oxycodone, hydrocodone, pethidine, hydromorphone and fentanyl. In any therapeutic method of the invention that requires down-regulation of GRP139, the GPR139 antagonist compounds to be used can be any agent that is capable of downregulating GPR139 expression or cellular level, or that is capable of inhibiting its biochemical activities. These include compounds (e.g., small organic molecules) that can specifically inhibit the GPCR signaling function of GPR139. GPR139 antagonists suitable for the invention can also be inhibitory polynucleotides or oligonucleotides such as siRNAs, shRNAs, antisense molecules and DNAzymes that are specific for the target gene sequence. They can also be antibodies or antibody fragments that specifically recognize the target GPR139 protein or a functional epitope or fragment of GPR139.

In some methods, the employed GPR139 antagonist can be an agent that specifically inhibits the signaling activities of GPR139. These include any GPR139 antagonist compounds that are known in the art. Examples of such known GPR139 antagonist compounds include Compounds NCRW0001-C02 and NCRW0005-F05, plus other structural scaffolds as described in Wang et al. (Acta Pharmacol. Sin. 36:874-8, 2015); and the triazolopyrimidine (e.g., Compound LP-114958) and sulfonamide (e.g., Compound LP-471756) related compounds as described in Hu et al. (J. Biomol. Screen 14: 789-97, 2009). These antagonist compounds can be readily obtained from commercial vendors, e.g., Axon Medchem (Reston, VA), Omeros Corp (Seattle, WA), and AdooQ Bioscience (Irvine, CA). Alternatively, they can be synthesized de novo via standard protocols of organic chemistry. In addition to known GPR139 antagonist compounds, additional GPR139 inhibitors that may be identified via various means, e.g., the screening methods described herein, can also be employed in the therapeutic methods of the invention.

In some other embodiments, the GPR139 antagonist used in the therapeutic methods of the invention can be inhibitory polynucleotides or nucleic acid molecules that specifically target a GPR139 encoding sequence, e.g., mRNA transcript. Such inhibitory polynucleotide molecules can be complementary, DNAzymes, antisense molecules, double stranded homologues, short interfering RNA (siRNA) molecules, or sequence specific single-stranded RNAs which form short hairpin structures, shRNA. In some embodiments, the employed inhibitory polynucleotides are siRNA or shRNA which can degrade the target sequence via RNA interference (RNAi) (see, e.g., Bass et al., Nature 411:428-29, 2001). Agents for RNA interference of GPR139 (e.g., siRNA oligonucleotides or shRNA vectors) can be obtained from or readily synthesized with reagents from commercial suppliers, e.g., Santa Cruz Biotechnology, Inc. (Santa Cruz, CA), Origene (Rockville, MD), GeneCopoeia (Rockville, MD), and Thermo Fisher Scientific (Carlsbad, CA). They can also be generated via routinely practiced laboratory techniques. For example, siRNA molecules suitable for the present invention can be generated by chemical synthesis or in vitro transcription using single-stranded DNA templates. See e.g., Yu et al., Proc. Natl. Acad. Sci. USA 99:6047-52, 2002; and Elbashir et al., Nature 411:494-98, 2001.

Other than RNA interference via siRNA or shRNA, some embodiments of the invention can employ other inhibitory polynucleotides to target GPR139. For example, DNAzymes can be used in the practice of the invention. DNAzymes are catalytic DNA molecules that are capable of cleaving either RNA (Breaker and Joyce, Chem. Biol. 1:223-9, 1994; and Santoro and Joyce, Proc. Natl. Acad. Sci. U.S.A. 94:4262-6, 1997) or DNA (Carmi et al., Chem. Biol. 3:1039-46, 1996) molecules. They are highly selective for the RNA sequence and as such can be used to down-regulate specific genes through, e.g., targeting the messenger RNA. Some other embodiments of the invention can employ antisense nucleic acid molecules that target GPR139. These are polynucleotide molecules that are complementary to a sense nucleic acid encoding a target polypeptide such as GPR139, e.g., complementary to the coding strand of a double-stranded cDNA molecule or complementary to an mRNA sequence. The antisense nucleic acid can be complementary to an entire coding strand, or to only a portion thereof, e.g., all or part of the protein coding region (or open reading frame). Suitable inhibitory polynucleotides for antagonizing GPR139 also encompass ribozymes. Ribozymes are catalytic RNA molecules with ribonuclease activity that are capable of cleaving a single-stranded nucleic acid, such as an mRNA, to which they have a complementary region. A ribozyme having specificity for a target nucleic acid molecule can be designed and produced in accordance with standard procedures well known in the art. See, e.g., Cech et al., U.S. Pat. No. 4,987,071; Cech et al., U.S. Pat. No. 5,116,742; Haselhoff and Gerlach, Nature 334:585-591, 1988; and Bartel and Szostak, Science 261: 1411-1418, 1993. These various inhibitory polynucleotides targeting GPR139 can also be obtained commercially or generated in house with standard techniques. For example, antisense nucleic acid molecules suitable for the invention can be readily constructed using chemical synthesis and enzymatic ligation reactions using procedures known in the art.

Some methods of the invention are directed to down-regulating MOR mediated signaling activities. In these methods, an agonist compound that is capable of promoting GPR139 GPCR function or expression can be used. For example, some of these methods of the invention can employ GPR139 agonist compounds that can stimulate GPCR function of GPR139. These methods are useful, e.g., to suppress or diminish reinforcing effects of opioids thus limiting their addictive liability. Many agonist compounds of GPR139 GPCR function are known in the art. For example, examples of specific GPR139 agonists include 2-(3,5-dimethoxybenzoyl)-N-(naphthalen-1-yl)hydrazine- 1-carboxamide (Nohr et al., Neurochem. Int. 102: 105-113, 2017), JNJ-63533054 (Liu et al., Mol. Pharmacol. 2015; 88:911-925), and Glycine benzamides (Dvorak et al., ACS Med. Chem. Lett. 2015; 6:1015-1018). Additional GPR139 agonists that may be employed in these methods of the invention include those described in Hu et al., J. Biomol. Screen. 14:789-797, 2009. Also suitable for these methods of the invention are GPR139 agonists that can be readily identified via the screening methods described herein, e.g., new scaffolds and small molecule compounds.

To enhance opioid analgesic effect, the GPR 139 modulating agents (e.g., antagonist compounds) may be administered directly to subjects in need of treatment. However, in an embodiment, a GPR139 modulating agent (e.g., an antagonist or agonist compound) is administered to the subjects in pharmaceutical compositions which comprise the GPR139 modulating agent and/or other active agents along with a pharmaceutically acceptable carrier, diluent or excipient in unit dosage form. Some examples of dosage unit forms are tablets, capsules, pills, powders, aqueous and nonaqueous oral solutions and suspensions, and patches. Pharmaceutically acceptable carriers are agents which are not biologically or otherwise undesirable, i.e., the agents may be administered to a subject along with a GPR139 modulating agent without causing any undesirable biological effects or interacting in a deleterious manner with any of the components of the pharmaceutical composition in which it is contained. The compositions can additionally contain other therapeutic agents that are suitable for treatments as described above. Pharmaceutical carriers enhance or stabilize the composition, or facilitate preparation of the composition. Pharmaceutically acceptable carriers include solvents, dispersion media, coatings, antibacterial and antifungal agents, isotonic and absorption delaying agents, and the like that are physiologically compatible. The pharmaceutically acceptable carrier should be suitable for various routes of administration described herein.

A pharmaceutical composition containing a GPR139 modulating agent (e.g., an antagonist or agonist compound) and other therapeutic agents described herein (e.g., an opioid drug) can be administered by a variety of methods known in the art. The routes and/or modes of administration vary depending upon the desired results. Depending on the route of administration, the active therapeutic agent may be coated in a material to protect the compound from the action of acids and other natural conditions that may inactivate the agent. Conventional pharmaceutical practice may be employed to provide suitable formulations or compositions to administer such compositions to subjects. Any appropriate route of administration may be employed, for example, but not limited to, oral administration, intravenous, parenteral, transcutaneous, subcutaneous, and intramuscular administration.

The GPR139 modulating agent (e.g., an antagonist or agonist compound) for use in the methods of the invention should be administered to a subject in an amount that is sufficient to achieve the desired therapeutic effect in a subject in need thereof. Typically, a therapeutically effective dose or efficacious dose of the GPR139 modulating agent is employed in the pharmaceutical compositions of the invention. Actual dosage levels of the active ingredients in the pharmaceutical compositions of the present invention can be varied so as to obtain an amount of the active ingredient which is effective to achieve the desired therapeutic response for a particular subject, composition, and mode of administration, without being toxic to the subject. The selected dosage level depends upon a variety of pharmacokinetic factors including the activity of the particular GPR139 modulating compound employed, or the ester, salt or amide thereof, the route of administration, the time of administration, the rate of excretion of the particular compound being employed. It also depends on the duration of the treatment, other drugs, compounds and/or materials used in combination with the employed GPR139 modulating compound, the age, gender, weight, condition, general health and prior medical history of the subject being treated, and like factors. Methods for determining optimal dosages are described in the art, e.g., Remington: *The Science and Practice of Pharmacy*, Mack Publishing Co., 20th ed., 2000.

Pharmaceutical compositions to be employed in the methods of the present invention can be prepared in accordance with methods well known and routinely practiced in the art. See, e.g., Remington: *The Science and Practice of Pharmacy*, Mack Publishing Co., 20th ed., 2000; and *Sustained and Controlled Release Drug Delivery Systems*, J. R. Robinson, ed., Marcel Dekker, Inc., New York, 1978. Pharmaceutical compositions can be manufactured under GMP conditions. Formulations for parenteral administration may, for example, contain excipients, sterile water, or saline, polyalkylene glycols such as polyethylene glycol, oils of vegetable origin, or hydrogenated napthalenes. Biocompatible, biodegradable lactide polymer, lactide/glycolide copolymer, or polyoxyethylene-polyoxypropylene copolymers may be used to control the release of the compounds. In some embodiments of the invention, the pharmaceutical composition to be employed can be a capsule for oral administration.

In another aspect, the invention provides methods for identifying novel agents that can be useful to reinforce opioid analgesic effects or to treat dependence associated with chronic opioid uses. Typically, test agents or candidate compounds are first assayed for their ability to modulate GPR139. Modulating compounds thus identified are then subject to further screening for ability to modulate opioid receptor signaling. The first step is intended to identify from the candidate agents a group of compounds that can modulate GPR139. In some embodiments, candidate agents can be screened for effects on expression or cellular level of GPR139 or an ortholog of GPR139. In some other embodiments, candidate agents can be first screened for ability to modulate one or more cellular activities (e.g., GPCR signaling function) of GPR139 or its orthologs. The test agents can be screened for ability to either up-regulate or down-regulate GPR139 in the first assay step. The second step of the screening methods of the invention serves to confirm that modulatory effect of the identified modulatory compounds on GPR139 would indeed lead to modulation of opioid receptor mediated signaling pathways. In some embodiments, modulating compounds identified in the first screening step are examined in the second step to identify compounds that specifically inhibit GPCR signaling activity of GPR139. In some other embodiments, they are screened to identify compounds that enhance GPCR signaling activity of GPR139. In some of these applications, compounds that have been identified to modulate GPCR function of GPR139 in the screening system can also be examined for their impact on GPCR function in a host that does not express GPR139. This step could confirm the compounds regulate GPCR function in a GPR139-dependent manner.

In both the first assaying step and the second testing step, either an intact GPR139 protein (e.g., human or mouse GPR139), GPR139 ortholog (e.g., FRPR-13 from *C. elegans*), or a functional fragment thereof, may be employed. Analogs or functional derivatives of GPR139 could also be used in the screening. The fragments or analogs that can be employed in these assays usually retain one or more of the biological activities of GPR139 (e.g., GPCR signaling function). Fusion proteins containing such fragments or analogs can also be used for the screening of test agents. Functional derivatives of GPR139 usually have amino acid deletions and/or insertions and/or substitutions while maintaining one or more of the bioactivities and therefore can also be used in practicing the screening methods of the present invention. A functional derivative can be prepared from GPR139 by proteolytic cleavage followed by conventional purification procedures known to those skilled in the art. Alternatively, the functional derivative can be produced by recombinant DNA technology by expressing only fragments of a GPR139 protein that retain one or more of their bioactivities. Any GPR139 sequence or orthologs known in the art can be employed in the practice of the invention. These include human GPR139 gene and orthologs from other species such as mouse and *C. elegans*. See, e.g., Takeda et al., FEBS Lett. 520: 97-101, 2002; Vassilatis et al., Proc. Natl. Acad. Sci. U.S.A. 100: 4903-4908, 2003; Matsuo et al., Biochem. Biophys. Res. Commun. 331: 363-369, 2005; Susens et al., Neuropharmacology 50: 512-520, 2006; Zimin et al., Genome Biol. 10: R42, 2009; and Liu et al., Mol. Pharmacol. 88: 911-925, 2015.

Various biochemical and molecular biology techniques or assays well known in the art can be employed to practice the screening methods of the present invention. Such techniques are described in, e.g., Seethala et al., *Handbook of Drug Screening*, Marcel Dekker; 1st Ed. (2001); Janzen, *High Throughput Screening: Methods and Protocols (Methods in Molecular Biology, 190)*, Humana Press; 1st Ed. (2002); Sambrook et al., *Molecular Cloning: A Laboratory Manual*, Cold Spring Harbor Press, N.Y., 3rd Ed. (2000); and Brent et al., *Current Protocols in Molecular Biology*, John Wiley & Sons, Inc. (ringbou ed., 2003). Further guidance to practice the screening methods of the present invention is provided below.

To identify potential MOR signaling modulators that promote opioid analgesic effects, biological function (e.g., GPCR signaling activities) or cellular level of GPR139 can be readily assessed in the first screening step via cellular assays that are known in the art or exemplified herein. For example, GPCR signaling activities of GPR139 can be examined with cell-based systems. For example, per some embodiments, *C. elegans* or transgenic *C. elegans* can be used to screen for molecules or genes that regulate FRPR-13 or GPR139; because these receptors dimerize, a useful screen identifies MOR modulatory compounds that target GPR139 or MOR. Additional assay systems of these types have been described in the art, e.g., Hu et al., J. Biomol. Screen. 14:789-797, 2009; Susens et al., Neuropharmacology. 50:512-520, 2006: Dvorak et al., ACS Med. Chem. Lett. 6:1015-1018, 2015; Isberg et al., Trends Pharmacol. Sci. 36:22-31, 2015; Liu et al., Mol. Pharmacol. 88:911-925, 2015; Shehata et al., Sci. Rep. 6:36681, 2016; and Wang et al., Acta Pharmacol. Sin. 36:874-81, 2015. In some embodiments, effect of candidate compounds on the cellular activities of GPR139 or orthologs can be monitored with cell lines that stably or transiently express GPR139. For example, cell lines expressing human GPR139 can be used to identify potential agonists and antagonists via the Fluo-4 Ca2+-assay as described in, e.g., Nohr et al., Neurochem. Int. 102: 105-113, 2017. In some embodiments, modulation of candidate agents on GPR139 can be examined with the high throughput screening platform based on intracellular calcium influx as described in Wang et al., Acta Pharmacol Sin. 36:874-8, 2015. In some other embodiments, potential modulators (e.g., antagonists) of GPR139 signaling function can be identified from candidate agents with the assay as described in Hu et al., which described use of HEK293F cells stably expressing human GPR139 for an AlphaScreen cAMP assay (Hu et al., J. Biomol. Screen. 14:789-797, 2009). In still some other embodiments, potential MOR signaling modulators can be identified from candidate agents via monitoring time resolved-fluorescence resonance energy transfer via the IP-One assay that was described in the art. See, e.g., Thomsen et al., Cell Calcium 51: 107-116, 2012; and Shehata et al., Sci. Rep. 6: 36681, 2016. Other cell based assays known in the art that can be employed to monitor GPR139 cellular or signaling activities in the screening methods of the invention include, e.g., Ca2+-Fluo-4 assay using CHO-k1 cell line stably expressing GPR139 (CHO-GPR139), [$^{35}$S]-GTPγS binding assay in membranes from COS7 cells, concentration-dependent calcium response in HEK293 cells, and calcium mobilization assay in HEK293 cells. See, e.g., Shehata et al., Sci. Rep. 6: 36681, 2016; Liu et al., Mol. Pharmacol., 88: 911-925, 2015; and Dvorak et al., PCT Patent Publication WO2014152917.

In addition to assays for screening agents that modulate biochemical activities of GPR139, the first step of the screening methods of the invention can also be directed to identifying candidate agents capable of modulating expression or cellular level of GPR139. Modulation of expression of GPR139 can be examined in a cell-based system by transient or stable transfection of an expression vector into cultured cell lines. Candidate compounds can be screened for activity in altering expression level of a gene encoding GPR139 in a cell, e.g., its mRNA level or protein level. These can be performed using methods well known and routinely practiced in the art, e.g., Sambook et al., supra; and Brent et al., supra. More typically, candidate compounds are assayed for ability to modulate expression of a reporter gene (e.g., luciferase gene) under the control of a transcription regulatory element (e.g., promoter sequence) of a gene encoding GPR139. Genes encoding GPR139 and various orthologs, including human GPR139, have been characterized in the art. Their transcription regulatory elements such as promoter sequences have all been delineated.

Candidate agents or test compounds that can be screened with methods of the present invention include compounds of any chemical classes. These include, e.g., organic compounds, polypeptides, polynucleotides, and phospholipids. In some embodiments, the employed candidate agents are aromatic compounds, heterocyclic compounds, benzodiazepines, oligomeric N-substituted glycines, or oligocarbamates. In some embodiments, the employed candidate agents are hormones, prostaglandins, fatty acids, steroids, purines, pyrimidines, derivatives, structural analogs or combinations thereof. In some methods, the test agents are small molecule organic compounds, e.g., chemical compounds with a molecular weight of not more than about 1,000 or 500. In various embodiments, high throughput assays are adapted and used to screen such small molecules. In some methods, combinatorial libraries of small molecule test agents as described above can be readily employed to screen for small molecule compound modulators of GPR139 signaling. A number of assays are available for such screening, e.g., assays as described in Schultz (1998) Bioorg. Med. Chem. Lett 8:2409-2414; Weller (1997) Mol. Divers. 3:61-70; Fernandes (1998) Curr. Opin. Chem. Biol. 2:597-603; and Sittampalam (1997) Curr. Opin. Chem. Biol. 1:384-91.

In some other embodiments, candidate agents to be screened with methods of the invention can be polypeptides, beta-turn mimetics, polysaccharides, phospholipids, hormones, prostaglandins, or steroids, polypeptides, saccharides, fatty acids, steroids. Some test agents are synthetic molecules, and others natural molecules. They can be obtained from a wide variety of sources including libraries of synthetic or natural compounds. Combinatorial libraries can be produced for many types of compound that can be synthesized in a step-by-step fashion. Large combinatorial libraries of compounds can be constructed by the encoded synthetic libraries (ESL) method described in WO 95/12608, WO 93/06121, WO 94/08051, WO 95/35503 and WO 95/30642. Peptide libraries can also be generated by phage display methods (see, e.g., WO 91/18980). Libraries of natural compounds in the form of bacterial, fungal, plant and animal extracts can be obtained from commercial sources or collected in the field. Known pharmacological agents can be subject to directed or random chemical modifications, such as acylation, alkylation, esterification, amidification to produce structural analogs.

Test agents or candidate compounds to be screened with methods of the present invention also include antibodies. In the first screening step, the candidate antibodies are examined for activity to specifically bind to GPR139. Antibodies that bind to GPR139 can then be tested for ability to modulate opioid receptor signaling, as described herein. The candidate antibodies can be monoclonal or polyclonal. Such antibodies can be generated using methods well known in the art. For example, the production of non-human monoclonal antibodies, e.g., murine or rat, can be accomplished by, for example, immunizing the animal with an antigenic polypeptide derived from GPR139 or its fragment (See Harlow & Lane, *Using Antibodies, A Laboratory Manual*, Cold Spring Harbor Laboratory Press, Cold Spring Harbor New York, 1998). Such an immunogen can be obtained from a natural source, by peptides synthesis or by recombinant expression. Humanized forms of mouse antibodies can be generated by linking the CDR regions of non-human antibodies to human constant regions by recombinant DNA techniques. See Queen et al., Proc. Natl. Acad. Sci. USA 86, 10029-10033 (1989) and WO 90/07861. Human antibodies can be obtained using phage-display methods. See, e.g., Dower et al., WO 91/17271; McCafferty et al., WO 92/01047. In these methods, libraries of phage are produced in which members display different antibodies on their outer surfaces. Antibodies are usually displayed as Fv or Fab fragments. Phage displaying antibodies with a desired specificity are selected by affinity enrichment. Human antibodies against GPR139 can also be produced from non-human transgenic mammals having transgenes encoding at least a segment of the human immunoglobulin locus and an inactivated endogenous immunoglobulin locus. See, e.g., Lonberg et al., WO93/12227 (1993); Kucherlapati, WO 91/10741 (1991).

As noted above, modulation of expression of GPR139 by test agents may also be detected by directly measuring the amount of RNA transcribed from a reporter gene under the control of a transcriptional regulatory element of GPR139. In these embodiments, the reporter gene may be any transcribable nucleic acid of known sequence that is not otherwise expressed by the host cell. RNA expressed from constructs containing a GPR139 promoter or enhancer may be analyzed by techniques known in the art, e.g., reverse transcription and amplification of mRNA, isolation of total RNA or poly A+ RNA, northern blotting, dot blotting, in situ hybridization, RNase protection, primer extension, high density polynucleotide array technology and the like. These techniques are all well known and routinely practiced in the art.

Once modulating compounds have been identified in the first screening step that alter GPR139 signaling activity or cellular level ("potential MOR modulators"), they are then subject to further test for activities in modulating MOR mediated opioid effects. This second screening step is useful to confirm that modulation of GPR139 by at least some of the identified compounds can indeed lead to modulation of MOR signaling activities (e.g., reinforced opioid effects). Typically, this screening step is performed in the presence of GPR139 on which the modulating compounds act. This screening step can be performed in vivo using animals that endogenously express MOR, e.g., mice model as exemplified herein. Alternatively, this screening step can be performed in transgenic animals that express a transgene encoding a heterologous MOR, e.g., tgMOR *C. elegans* as exemplified herein.

Modulation of the identified candidate compounds from the first screening step on MOR mediated signaling or opioid effects can be examined using methods well known in the art. In some embodiments, the compounds can be examined with in vitro assays to confirm their effect on MOR signaling. For example, as exemplified herein, the second screening step can employ an assay to examine activation of G protein gated inwardly rectifying K+ (GIRK) channels mediated by MOR signaling. Alternatively, effect of the compounds on MOR-mediated activation of G proteins can be examined via a bioluminescence resonance energy transfer (BRET) assay as exemplified herein.

In some other methods, the second screening step can utilize in vivo animal models to confirm that the identified compounds indeed possess ability to modulate promote MOR signaling or MOR mediated opioid analgesic effect. As exemplified herein, the in vivo assay system can be one that examine behavior response in mice to opioid signaling. Specifically, upon administering to mice the identified compounds from the first screening step, the assay in the second screening step can be directed to selecting any of the compounds that can produce increased morphine analgesia in the animal, including maximal response and duration of analgesic effect. Readout of the second screening step in the animal can also be diminished withdrawal symptoms or reward (opioid reinforcement), as exemplified herein. In addition to mammalian system such as mice, in vivo assay in the second screening step can also use other kinds of animal models. As exemplified herein, the screening methods of the invention can employ transgenic *C. elegans* expressing a mammalian MOR receptor (e.g., human MOR). Effect of the identified compounds on MOR signaling can be monitored via, e.g., selecting any of the compounds that can lead to an enhanced (when selecting for MOR agonists) or reduced (when selecting for MOR antagonists) sensitivity to opioid drugs in the transgenic animal. In any of the in vivo assay systems employed in the second screening step, the animals can be administered with the potential MOR-modulating compounds prior to, simultaneously with, or subsequent to administration with an opioid drug, such as morphine or fentanyl.

EXAMPLES

The following examples are provided to further illustrate the invention but not to limit its scope. Other variants of the invention will be readily apparent to one of ordinary skill in the art and are encompassed by the appended claims.

Example 1 Transgenic *C. elegans* Platform for Dissection of Opioid Signaling Mechanisms To study the effect of MOR using a behavioral platform that can be scaled to cover an entire genome, we generated transgenic *C. elegans* (tgMOR) that express mammalian MOR throughout the nervous system (FIG. 1A, B). Since opioid agonists exert robust effects on motor activity in mammals, we first assessed the effects of MOR activation on *C. elegans* locomotion. Exposure of tgMOR worms to fentanyl, a selective MOR agonist, drastically reduced their movement (FIG. 1C). Quantitation showed fentanyl significantly inhibits thrashing of tgMOR animals over time (FIG. 1D). tgMOR animals rapidly recovered from paralysis in the presence of fentanyl indicating conservation of receptor desensitization mechanisms (FIG. 1D). Importantly, fentanyl did not affect non-transgenic animals, indicating that changes in motor activity result from activation of transgenic MOR (FIG. 1C, D).

Figure 1G:
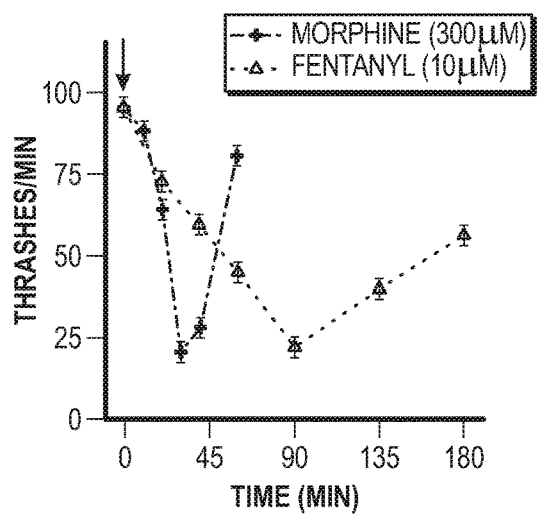
Figure 1H:
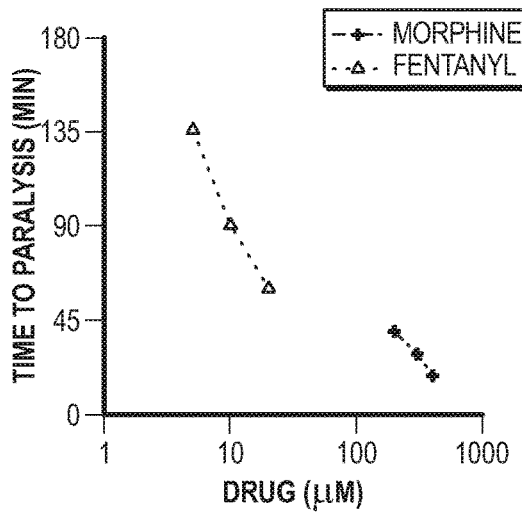
Figure 1I:
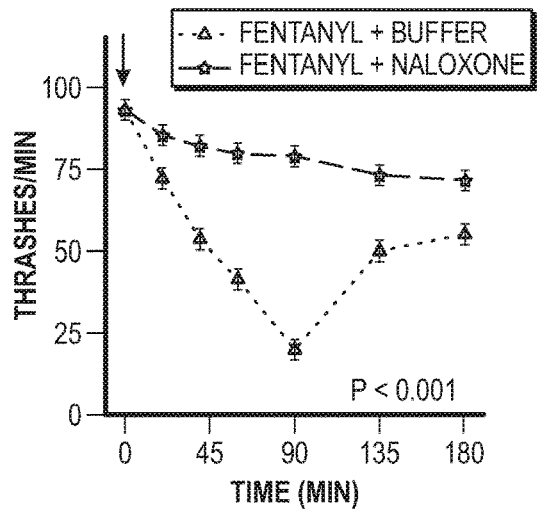
Figure 6A:
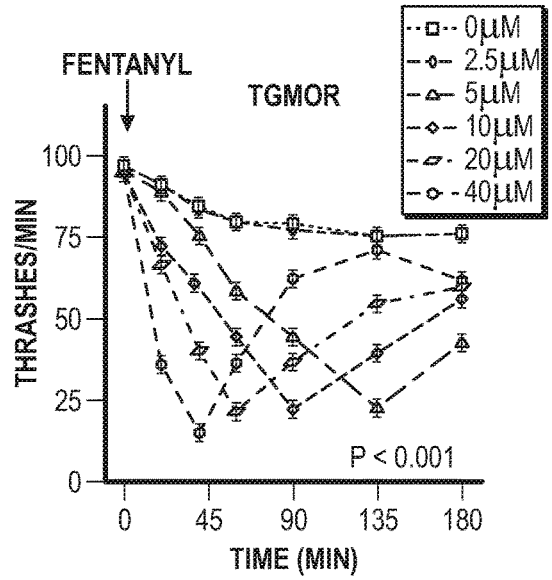
FIG. 6 shows expanded dose effects showing tgMOR; rsbp-1 animals are hypersensitive to fentanyl and morphine. Time course of fentanyl concentrations inducing paralysis on (A) tgMOR or (B) tgMOR; rsbp-1 mutants. (C) Dose response showing tgMOR; rsbp-1 mutants are hypersensitive to fentanyl. Time course of morphine concentrations inducing paralysis in (D) tgMOR and (E) tgMOR; rsbp-1 mutants. (F) Dose response showing tgMOR; rsbp-1 mutants are hypersensitive to morphine. Significance tested using two-way ANOVA.
Figure 6B:
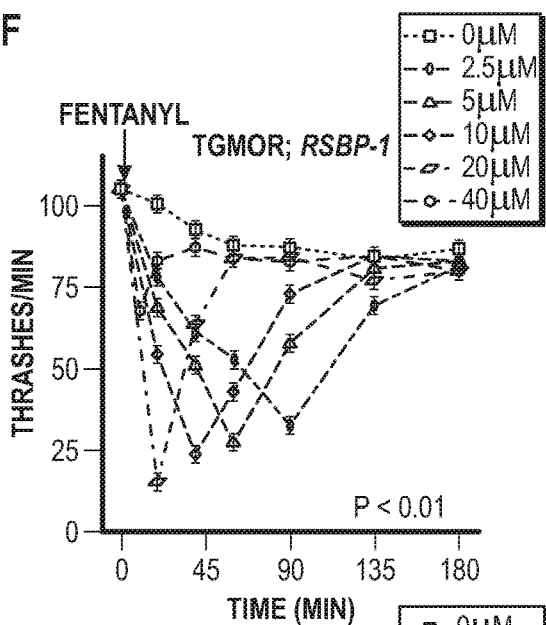
Figure 6C:
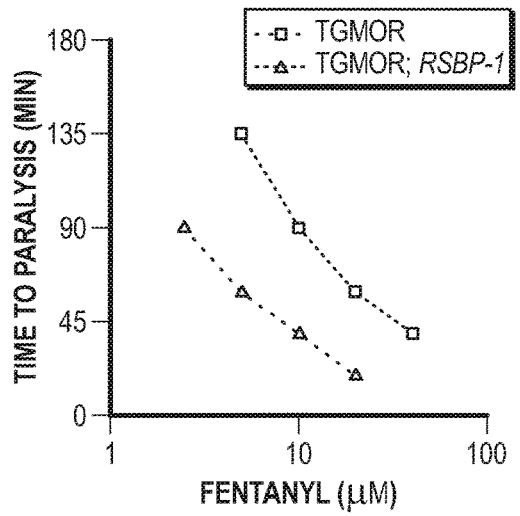
Figure 6D:
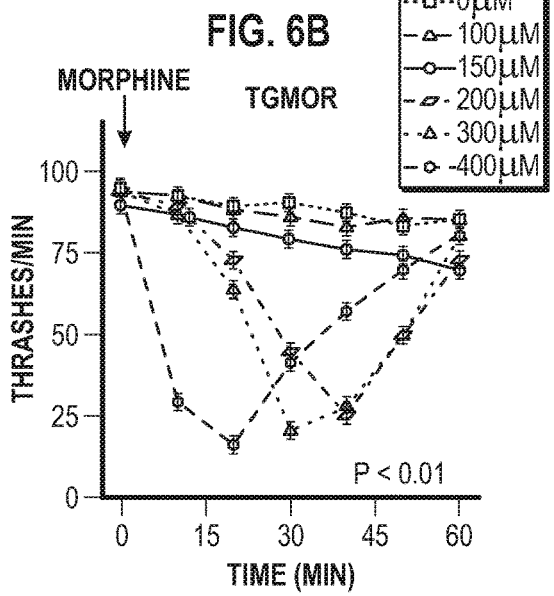

Interestingly, increasing concentrations of fentanyl accelerated the speed of both response onset and recovery, but did not alter extent or duration of paralysis (FIG. 1E, F; FIG. 6A). This suggests that MOR desensitization in *C. elegans* occurs on the timescale of the response generation and as a result, the strength of MOR signaling is reflected in onset timing rather than response magnitude. To further validate this model, we studied responses to morphine, a full MOR agonist with a unique desensitization profile (28, 29). Indeed, morphine produced a similar magnitude of effect as fentanyl but had a distinct temporal profile with faster response onset and more rapid recovery (FIG. 1G; FIG. 6D). Consistent with morphine having lower potency on MOR (29) approximately 50-fold higher concentration of morphine was required for maximal effect compared to fentanyl (FIG. 1H). Finally, pretreatment of tgMOR animals with naloxone, a MOR-selective antagonist, abolished the effect of fentanyl providing further validation (FIG. 1I).

Figure 6E:
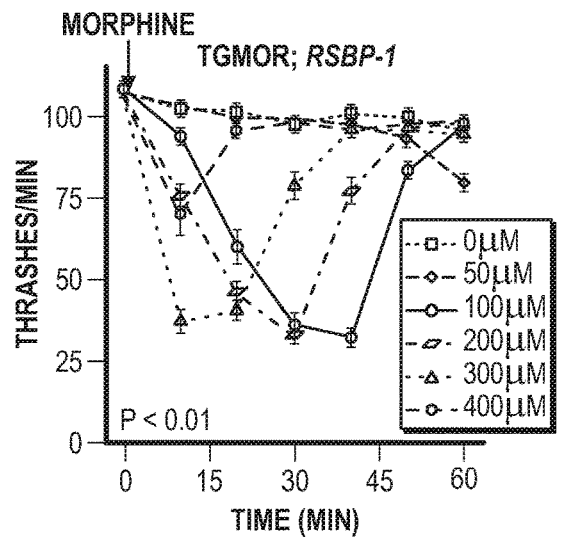
Figure 6F:
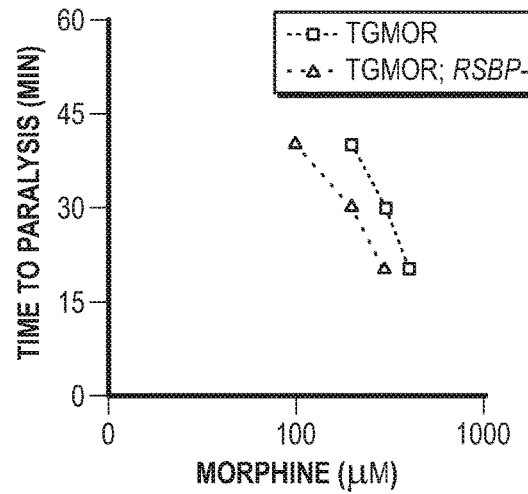
Figure 7A:
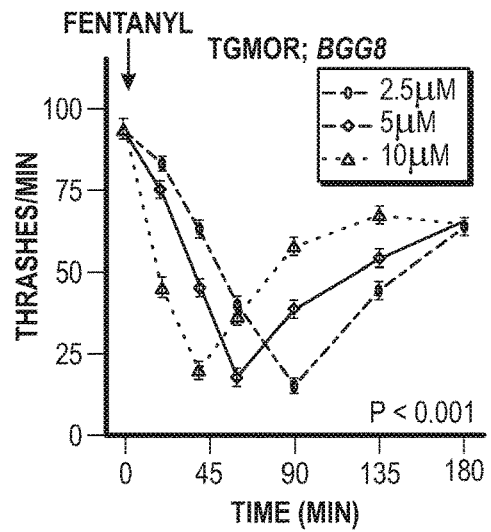
FIG. 7 shows dose response showing tgMOR; bgg8 and tgMOR; bgg9 mutants are hypersensitive to fentanyl. (A) Time course of fentanyl concentrations inducing paralysis on tgMOR: bgg8 animals. (B) Dose response showing tgMOR; bgg8 mutants are hypersensitive to fentanyl. (C) Time course of fentanyl concentrations inducing paralysis on tgMOR; bgg9 animals. (D) Dose response showing tgMOR; bgg9 mutants are hypersensitive to fentanyl. Significance tested using two-way ANOVA.
Figure 7B:
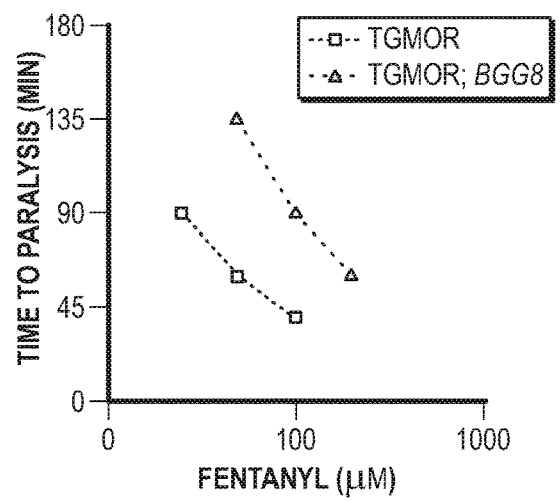
Figure 7C:
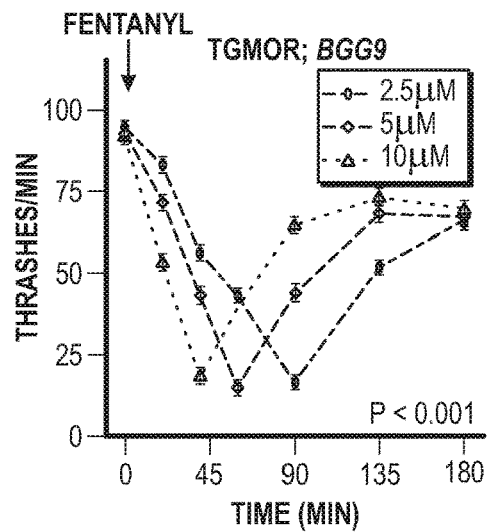
Figure 7D:
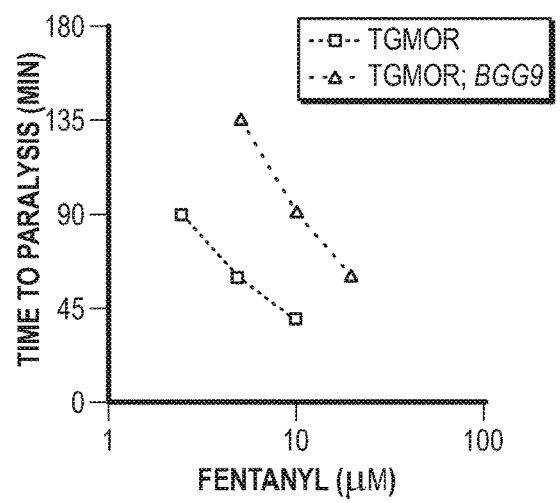

To probe whether conserved molecular mechanisms control opioid signaling, we evaluated opioid-induced behavior in tgMOR animals lacking RSBP-1. RSBP-1 is orthologous to mammalian R7BP, a subunit of the GAP complex that negatively regulates MOR signaling in mice (FIG. 1A) (30, 31). Remarkably, rsbp-1 loss-of-function mutants carrying tgMOR reached maximum paralysis and recovered more quickly than wild-type tgMOR animals treated with fentanyl (FIG. 1J; FIG. 6B) or morphine (FIG. 1K; FIG. 6E). Dose-response studies showed a prominent left-ward shift in concentration dependence for both fentanyl and morphine (FIG. 6C, F). Thus, tgMOR; rsbp-1 mutants are hypersensitive to opioids, an outcome similar to R7BP deletion in mice (31).

Taken together, these observations indicate that opioid signaling via MOR can be effectively modeled in *C. elegans* producing behavioral reactions mediated by conserved GPCR signaling machinery that function independent of organism-specific neuronal circuitry.

Example 2 Forward Genetic Screen for Opioid Sensitivity Modulators in tgMOR Platform The robust effects of opioids on tgMOR *C. elegans* and the molecular conservation of regulatory mechanisms prompted us to adopt this platform for an unbiased, forward genetic screen for novel regulators of opioid signaling. We focused on identifying mutants with increased opioid sensitivity to uncover negative regulators of MOR signaling.

Figure 1J:
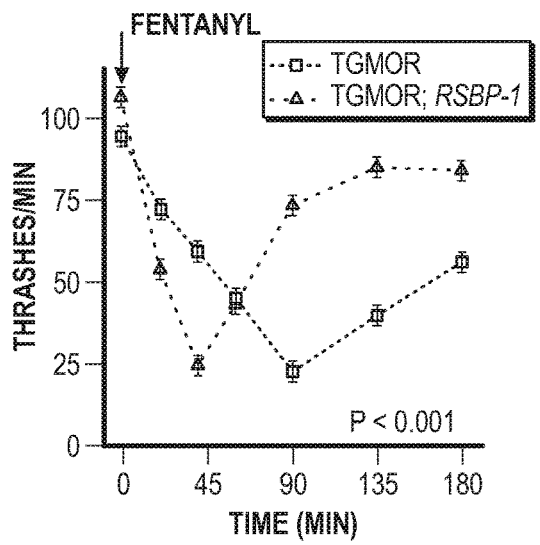
Figure 1K:
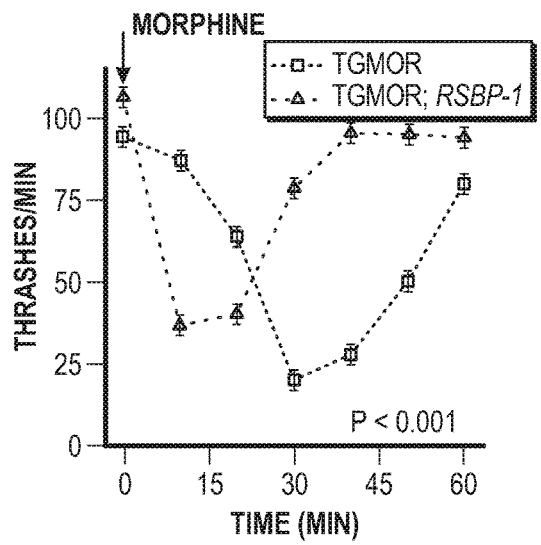

Key to the design of our screen was the observation that greater opioid response leads to faster paralysis and more rapid recovery. Thus, hypersensitive animals like rsbp-1 recover faster from the same drug dose than wild-type tgMOR animals (FIG. 1J, K). As a result, plate-based, bulk segregation was used to isolate hypersensitive mutants based on quicker recovery from opioid-induced paralysis and escape to harvest zones (FIG. 2A). Assay optimization utilizing a mixture of tgMOR animals and hypersensitive tgMOR; rsbp-1 mutants showed that primary screening with morphine followed by secondary screening with fentanyl minimized false positive rates (FIG. 2A).

For the full-scale screen, we mutagenized ~2,500 tgMOR animals, evaluated ~600,000 animals, and identified ~900 mutants with abnormal sensitivity to both morphine and fentanyl (FIG. 2B). Secondary evaluation in liquid thrashing assays with fentanyl eliminated false positives, identified mutants that lost opioid sensitivity, and confirmed a small number of hyper-sensitive mutants (FIG. 2C). We focused our efforts on comprehensive testing of opioid-induced behaviors of two candidates: bgg8 and bgg9 that had normal overall morphology and behavior in the opioid naïve state. Both mutants reached paralysis significantly faster than wild-type tgMOR worms (FIG. 2D, E). Additional dose-response studies showed a leftward shift in fentanyl-induced paralysis indicating that bgg8 and bgg9 mutants are hypersensitive to opioids (FIG. 7A-D).

Example 3 Orphan Receptor FRPR-13 Negatively Regulates MOR Signaling

Figure 3A:
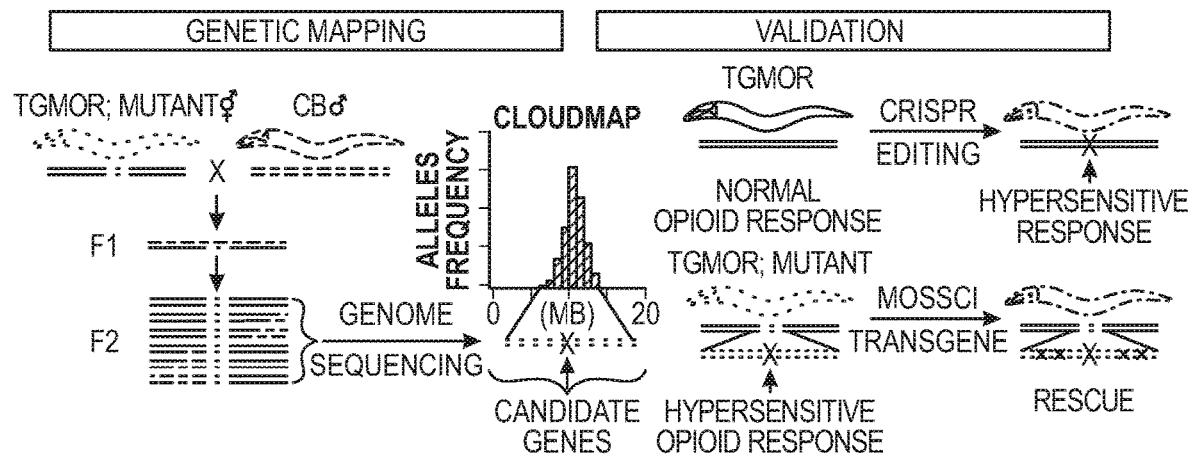
FIG. 3 shows that orphan receptor FRPR-13 negatively regulates MOR signaling. (A) Flowchart for whole-genome sequencing and mapping tgMOR mutants from opioid screen. (B) Targeted CRISPR/Cas9-based editing validates egl-19 as gene responsible for hypersensitivity to fentanyl in bgg-8 mutant. (C) Targeted CRISPR/Cas9-based editing validates frpr-13 as gene causing hypersensitivity to fentanyl in bgg9 mutant. (D) Transgenic expression of FRPR-13 using native or neuronal promoters rescues fentanyl hypersensitivity in tgMOR; bgg9 animals. (E) Transgenic expression of human GPR139 rescues hypersensitivity in tgMOR; bgg9 animals. Arrows denote drug application. Significance tested using two-way ANOVA. * $p<0.001$ and ns=not significant

To identify genetic lesions causing hypersensitivity, we used whole-genome sequencing and SNP Cloud Mapping (32) after mating tgMOR hypersensitive mutants with a CB reference strain (FIG. 3A). This process combined with phenotypic selection isolated genomic regions of interest containing approximately 6-8 different lesions per mutant. To determine which lesion caused opioid hypersensitivity, we CRISPR/Cas9 edited single mutations into candidate genes of wild-type tgMOR animals (FIG. 3A).

Figure 3B:
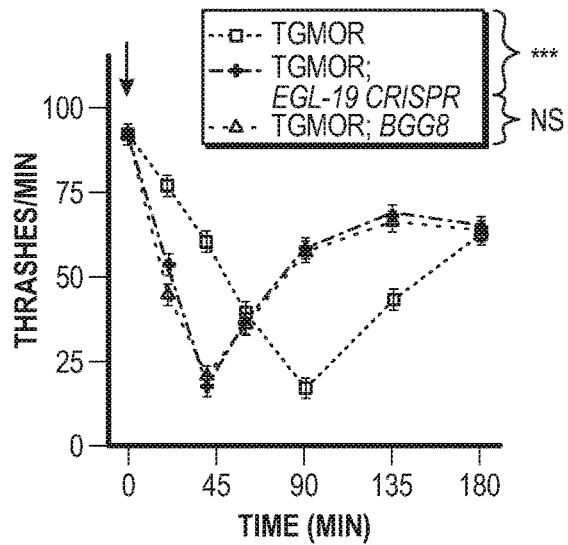
Figure 8A:
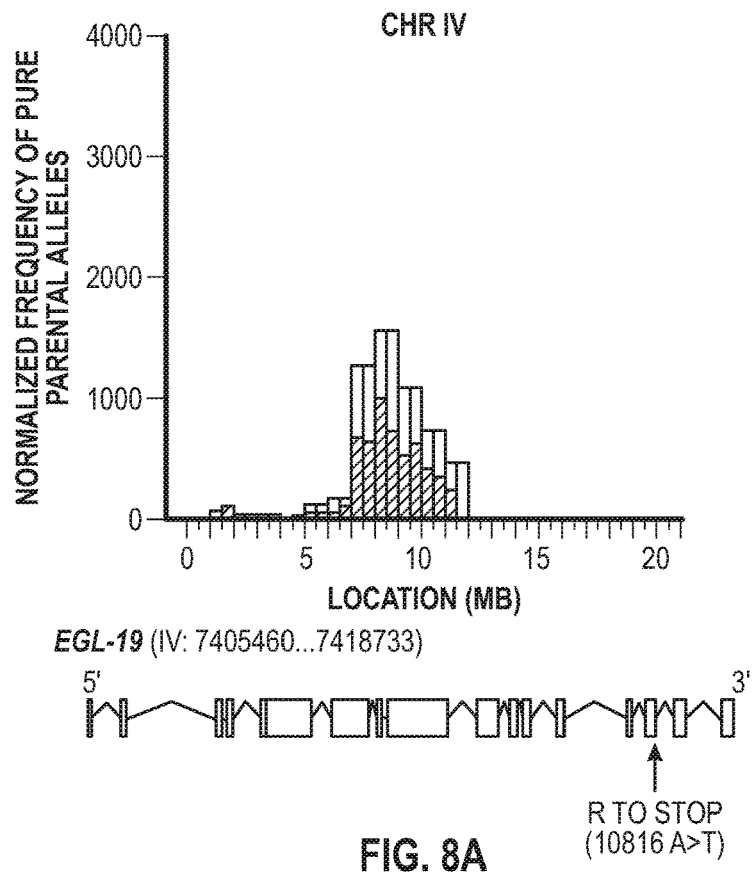
FIG. 8 shows whole genome sequencing and mapping of mutations in tgMOR; bgg8 and tgMOR; bgg9. (A) Plot showing mapped region of chromosome IV (red and grey bars) containing bgg8. Gene diagram showing mutation in egl-19 contained in mapped region. (B) Mapping plot for bgg9 (red and grey) on chromosome V. Gene diagram showing mutation in frpr-13 contained in mapped region.
Figure 9A:
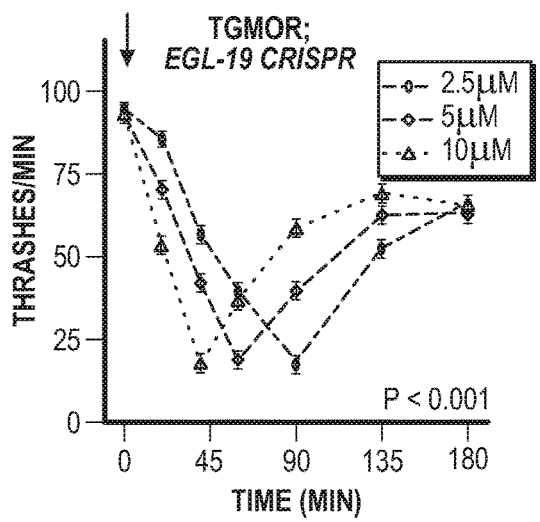
FIG. 9 shows that CRISPR editing shows mutations in egl-19 and frpr-13 cause hypersensitivity to fentanyl. (A) Time course of fentanyl concentrations inducing paralysis on tgMOR; egl-19 CRISPR animals. (B) Fentanyl dose response showing tgMOR; egl-19 CRISPR and tgMOR; bgg8 both cause hypersensitivity to fentanyl (leftward shift) compared to wt tgMOR animals. (C) Time course of fentanyl concentrations inducing paralysis on tgMOR; frpr-13 CRISPR animals. (D) Fentanyl dose response showing tgMOR; frpr-13 CRISPR and tgMOR; bgg9 both cause hypersensitivity to fentanyl. Arrows denote 10 µM fentanyl application. Significance tested using two-way ANOVA.
Figure 9B:
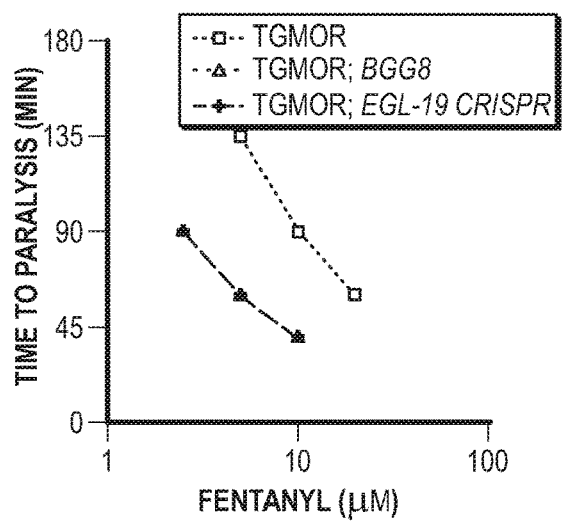

For tgMOR; bgg8 animals, we identified a lesion in the calcium channel egl-19 that introduces a premature stop codon and likely results in loss of function (FIG. 8A). CRISPR/Cas9 editing the same egl-19 mutation into parental tgMOR animals confirmed egl-19 affects opioid sensitivity (FIG. 3B; FIG. 9A, B). Notably, egl-19 is homologous to L-type $Ca^{2+}$ channels in mammals and extensive evidence documents that L-type $Ca^{2+}$ blockers potentiate the nociceptive properties of opioids in a clinical setting (33, 34). These observations demonstrate the power of our forward genetic screen to identify conserved regulators of MOR signaling with translational potential.

Figure 3C:
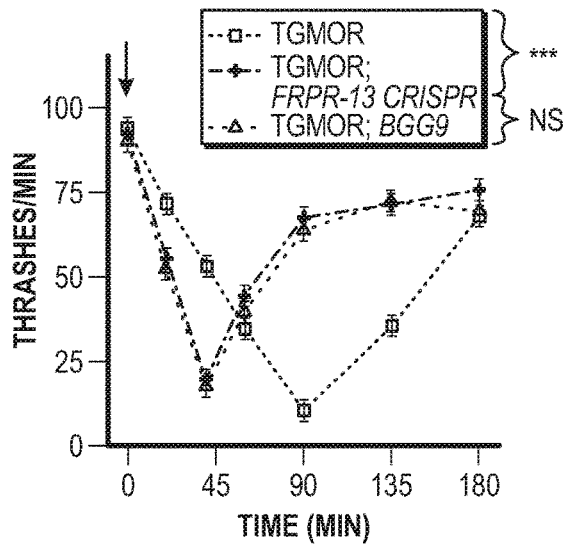
Figure 3D:
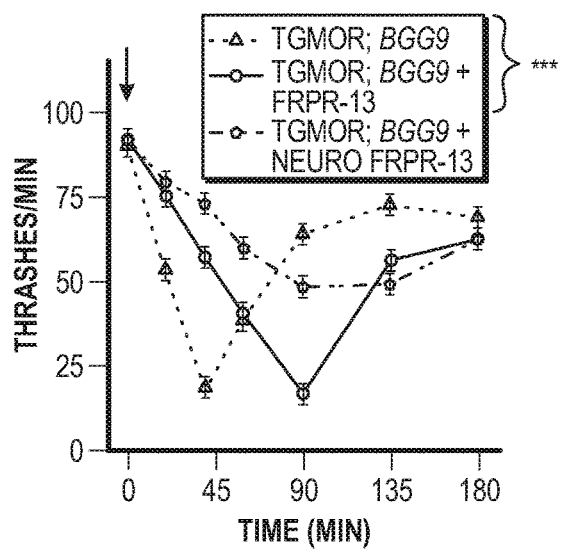
Figure 8B:
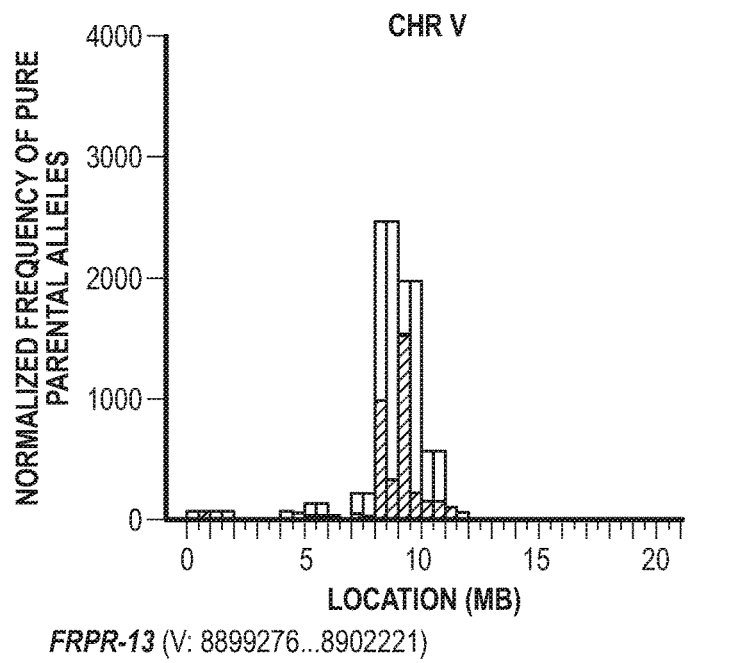
Figure 9C:
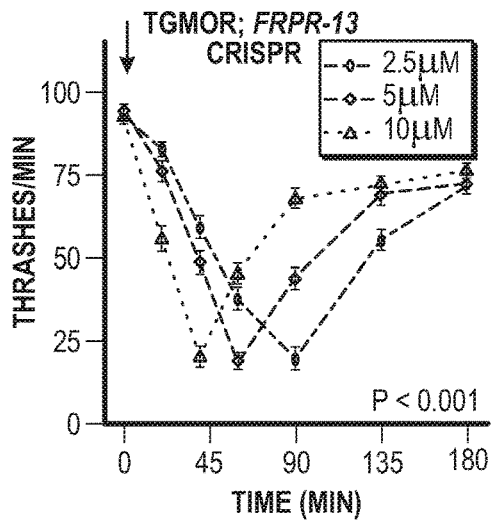
Figure 9D:
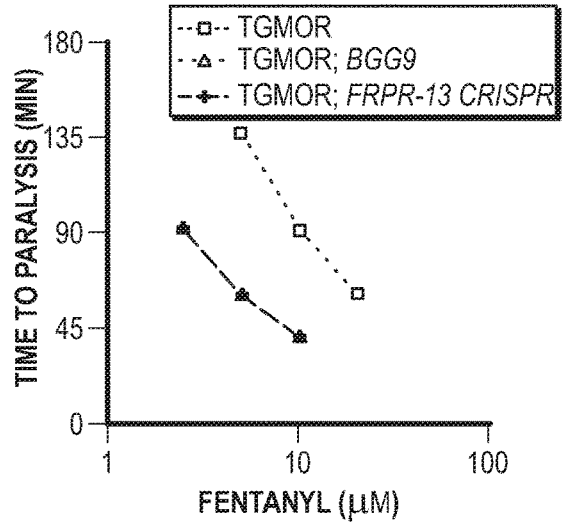
Figure 10A:
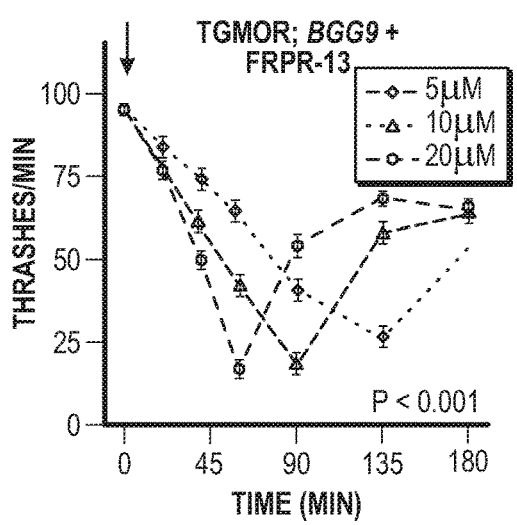
FIG. 10 shows that transgenic FRPR-13 rescues fentanyl hypersensitivity of tgMOR; bgg9 mutants. (A) Time course of fentanyl concentrations inducing paralysis on tgMOR; bgg9 animals carrying a single copy of FRPR-13 driven by its native promoter. (B) Fentanyl dose response showing hypersensitivity (leftward shift) of tgMOR; bgg9 animals is rescued by transgenic FRPR-13. Significance tested using two-way ANOVA.
Figure 10B:
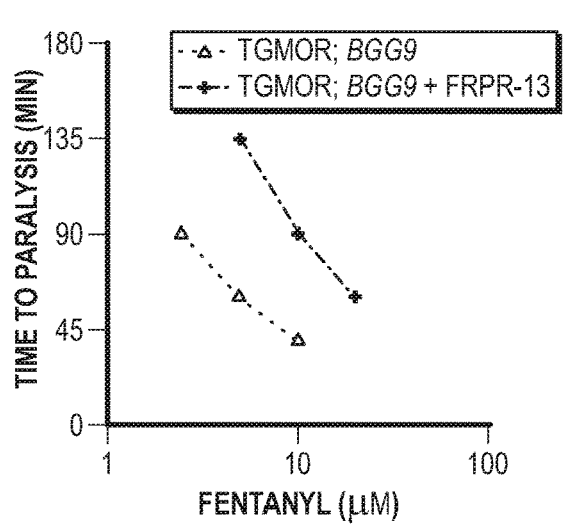

Another hypersensitive mutant, bgg9, contained a premature stop in frpr-13 which encodes an unstudied orphan GPCR (FIG. 8B). CRISPR/Cas9 editing this lesion into tgMOR increased sensitivity to fentanyl confirming frpr-13 affects opioid sensitivity (FIG. 3C; FIG. 9C, D). Since the function of FRPR-13 is unknown, we further validated that it regulates opioid responses with transgenic rescue experiments. Transgenic FRPR-13 expression using Mos single copy insertion (MosSCI) and the native frpr-13 promoter significantly rescued hypersensitivity in frpr-13 (bgg8) mutants (FIG. 3D; FIG. 10). Furthermore, pan-neuronal MosSCI expression of FRPR-13 also rescued hypersensitivity in frpr-13 (bgg8) mutants (FIG. 3D). These results indicate the FRPR-13 receptor alters sensitivity to opioids at a behavioral level.

Figure 3E:
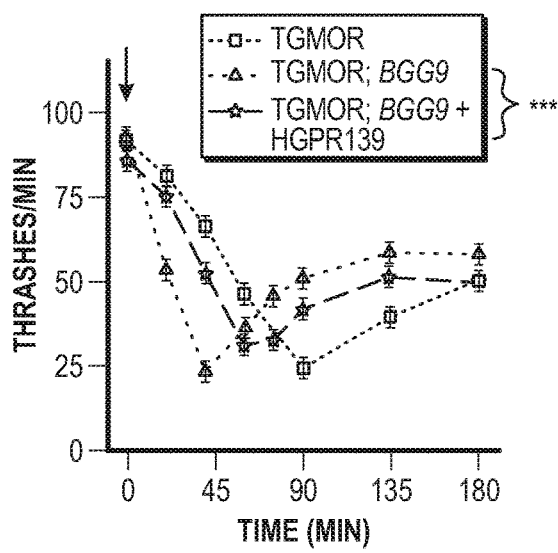
Figure 11:
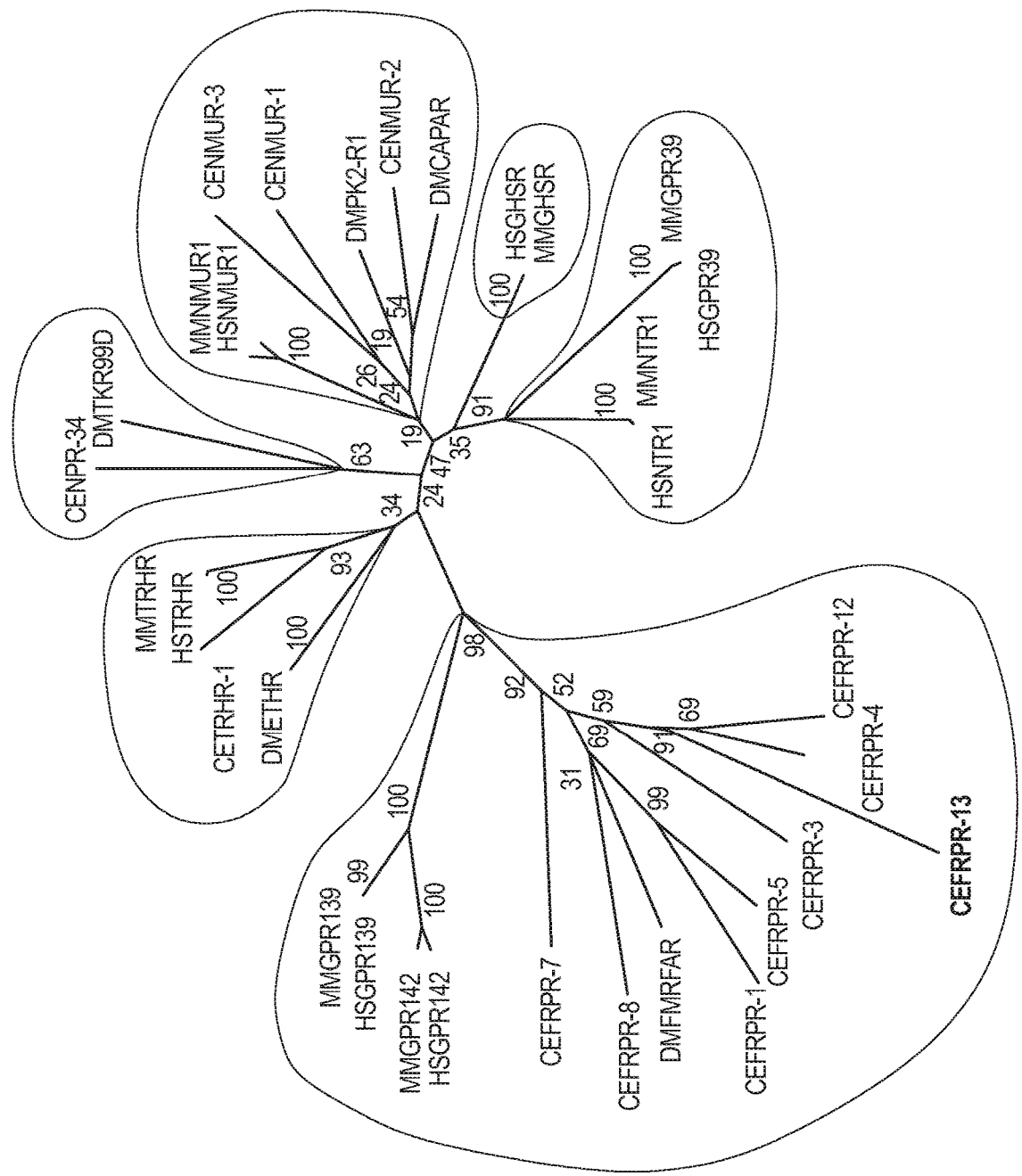
FIG. 11 shows that FRPR-13 is one of several *C. elegans* receptors with homology to mouse and human GPR139. Molecular phylogenetic analysis of different receptors in the Neurotensin/GPR139 cluster of GPCRs from human (black), mouse (green), fly (blue) and *C. elegans*. Phylogenetic tree generated using protein sequences and MEGA 5 software. *C. elegans* FRPR-13 is part of an expanded group of receptors in worms with closest homology to human and mouse GPR139 and GPR142.
Figure 12:
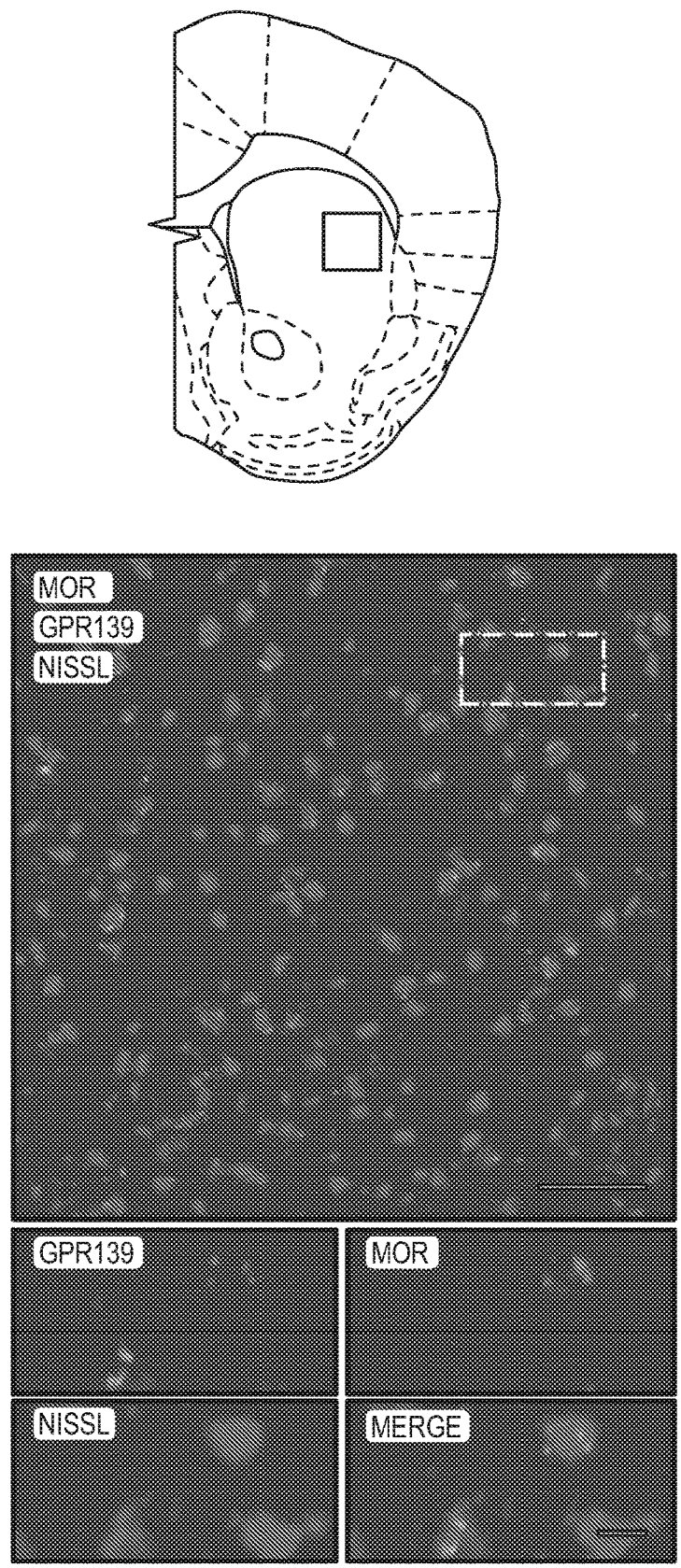
FIG. 12 shows that GPR139 is coexpressed with MOR in striatum. In situ hybridization showing extensive coexpression of MOR and GPR139 in neurons of the striatum. Squares show region imaged.

Phylogenetic analysis revealed that FRPR-13 belongs to a large neuropeptide receptor group in *C. elegans* that is homologous to two mammalian orphan GPCRs, GPR139 and GPR142 (FIG. 11). GPR139 and 142 are in a distinct subfamily of class A orphan receptors (35). Given that nothing is known about FRPR-13 and there is no prior connection between GPR139/142 and opioid signaling, we explored the functional conservation of these receptors. We focused on GPR139 for its neuronal specific expression in mammals, in contrast to GPR142 which is predominantly found in the periphery (36, 37). Transgenic expression of human GPR139 in tgMOR; bgg9 worms with disrupted FRP-13 significantly rescued hypersensitivity to fentanyl (FIG. 3E). This indicates GPR139 is a functional ortholog of FRPR-13, and GPR139 can inhibit MOR signaling in vivo.

Example 4 GPR139 Inhibits MOR Signaling

Figure 4A:
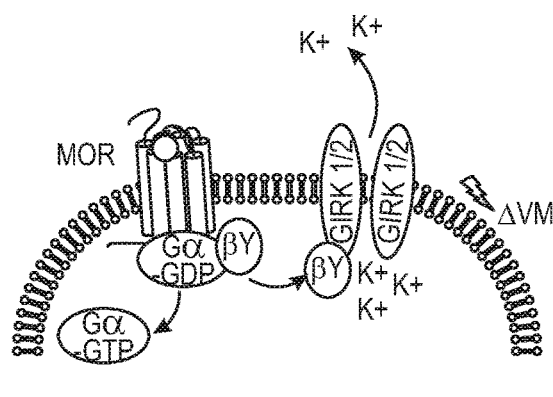
FIG. 4 shows that GPR139 inhibits MOR signaling. (A) Experimental design for evaluating MOR signaling via its effector GIRK. The Gβγ subunits released upon MOR activation by morphine open GIRK channels to produce membrane hyperpolarization (Vm) measured with voltage sensitive dye. (B) Effect of GPR139 coexpression on MOR-induced kinetics of membrane potential change. (C) Quantification of Vm amplitude in the presence and absence of GPR139. (D) Experimental design for evaluating MOR signaling to G proteins by the BRET assay that monitors MOR-mediated release of Gβγ subunits. (E) Effect of GPR139 coexpression on kinetics of G protein activation by morphine activation of MOR. (F) Quantification of maximal BRET response amplitude in presence and absence of GPR139. Significance tested one-way ANOVA with Dunnett's post-hoc. * $p<0.001$, ** $p<0.01$, * $p<0.05$
Figure 4B:
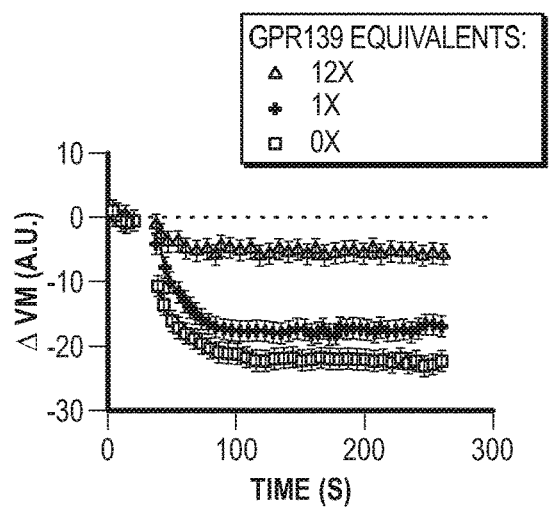
Figure 4C:
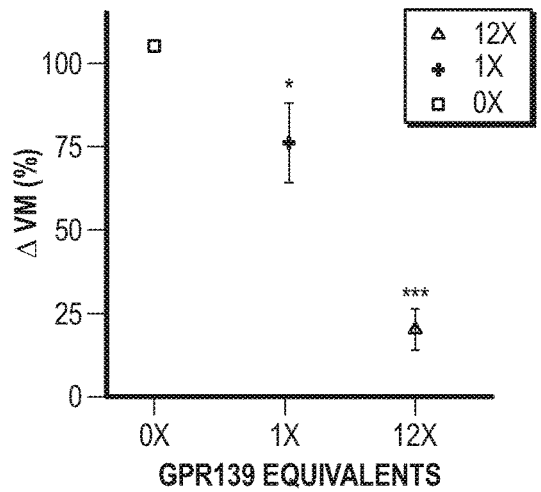
Figure 4D:
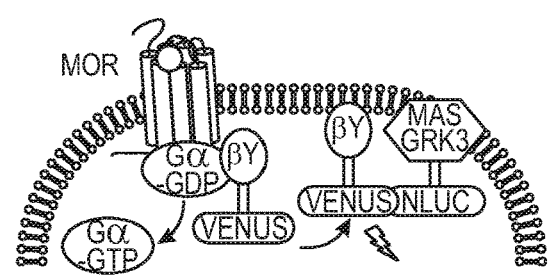
Figure 4E:
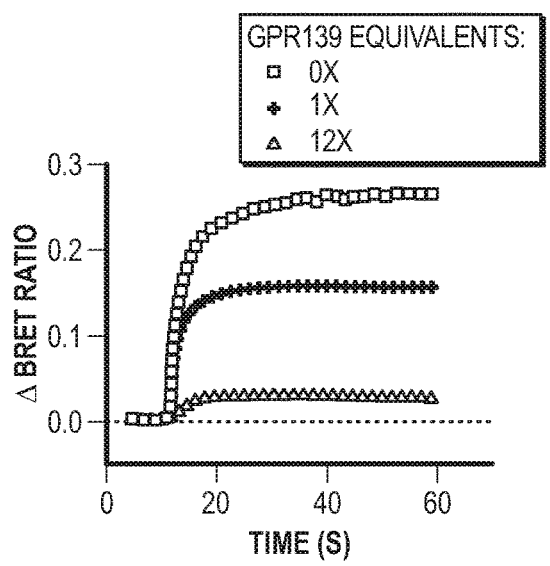
Figure 4F:
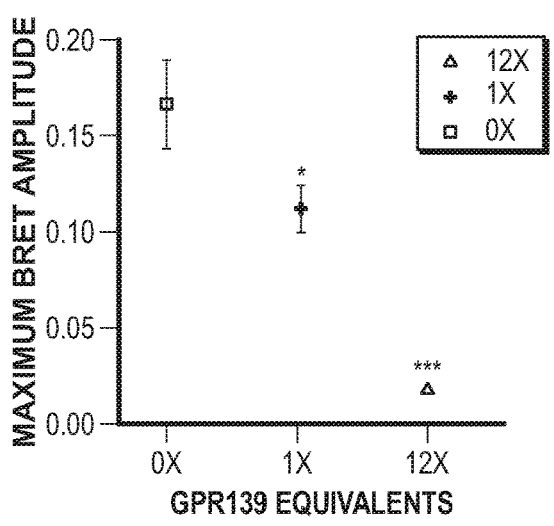

Next, we turned to a cell-based system to evaluate how GPR139 influences MOR signaling. We reconstituted the prevalent MOR signaling pathway to G protein gated Inwardly Rectifying K+ (GIRK) channels. GIRK channel opening by Gβγ subunits, which are liberated upon MOR activation, accounts for much of the inhibitory effects of opioids due to hyperpolarization of membrane potential (FIG. 4A) (38). Indeed, opioid activation of MOR drove rapid and robust changes in membrane voltage (FIG. 4B). Introduction of GPR139 cDNA in equivalent concentrations to MOR inhibited morphine-induced hyperpolarization, whereas overexpression of GPR139 at high levels nearly abolished GIRK activation (FIG. 4B, C). To further understand the mechanism by which GPR139 inhibits MOR signaling, we tested how GPR139 influences MOR-mediated activation of G proteins using a Bioluminescence Resonance Energy Transfer (BRET) strategy (FIG. 4D) (39). Morphine produced a rapid BRET response reflecting rearrangement in Gαo-Goγ heterotrimers induced by MOR activation (FIG. 4E). Coexpression of GPR139 inhibited MOR-induced G protein activation at both low and high expression levels (FIG. 4E, F). Together, these results indicate that GPR139 exerts inhibitory effects on MOR in a cell autonomous fashion.

Example 5 GPR139 Controls Behavioral Sensitivity of Mice to Opioid Drugs

Figure 5A:
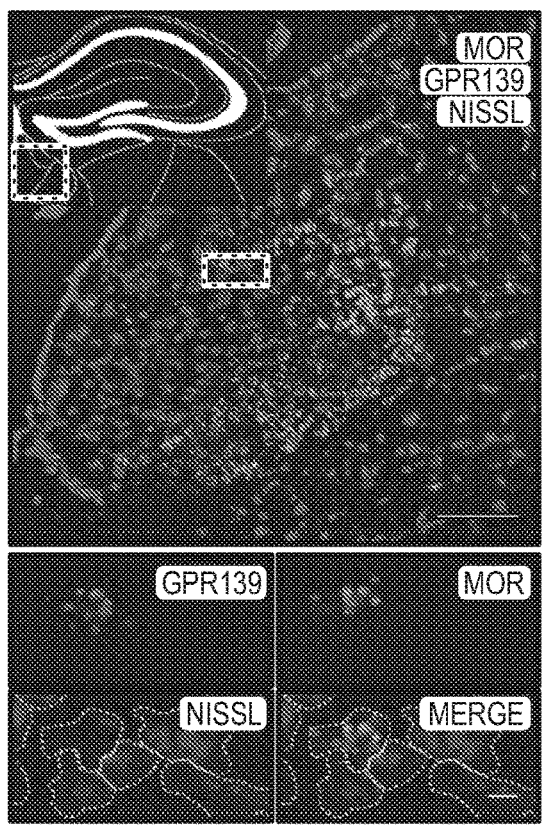
FIG. 5 shows that GPR139 controls behavioral sensitivity of mice to opioid drugs. (A) In situ hybridization showing extensive coexpression of MOR and GPR139 in neurons of the habenula. (B) Design of Gpr139 knockout allele completely disrupts protein expression. (C) Hot plate assay showing increased dose-dependent, anti-nociceptive effects of morphine in Gpr139$^{-/-}$ mice. (D) Gpr139$^{-/-}$ animals have increased duration of morphine analgesia in hot plate assay. (E) Conditioned place preference paradigm showing increased reward in Gpr139$^{-/-}$ mice. (F) GPR139 knockouts have decreased behavioral responses and weight loss to naloxone-precipitated somatic withdrawal following chronic morphine exposure. Significance tested using two-way ANOVA or t-test as described in Methods. * $p<0.001$,  $p<0.01$, * $p<0.05$
Figure 5B:
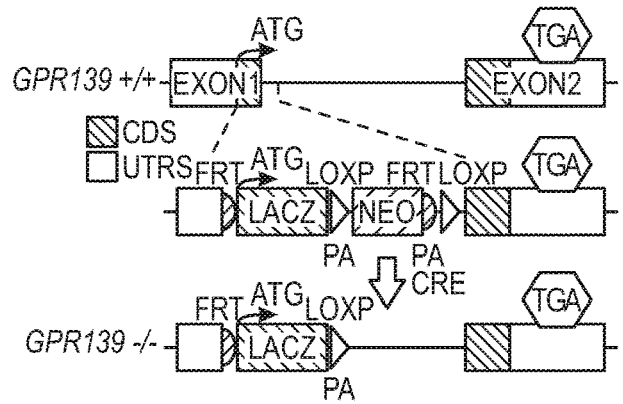
Figure 5C:
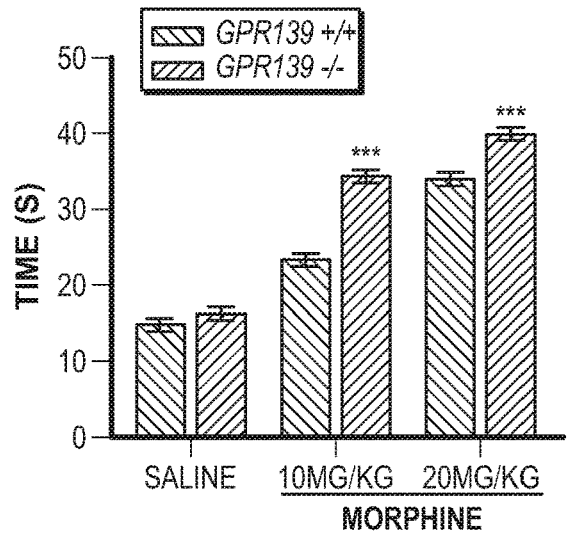
Figure 5D:
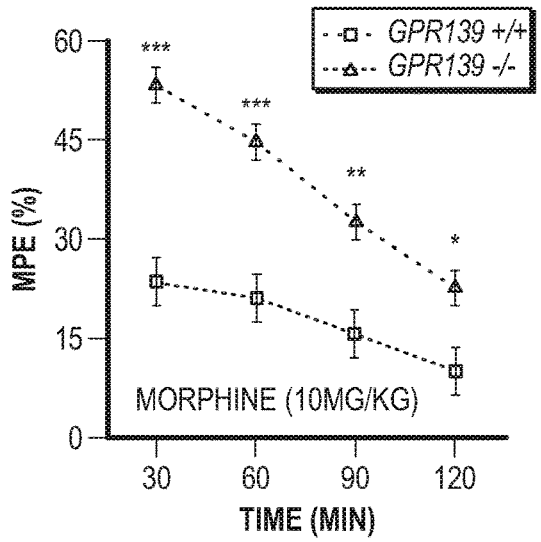
Figure 5E:
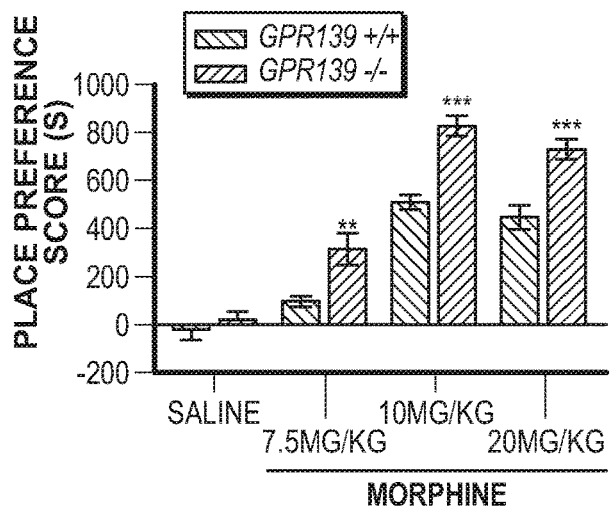
Figure 5F:
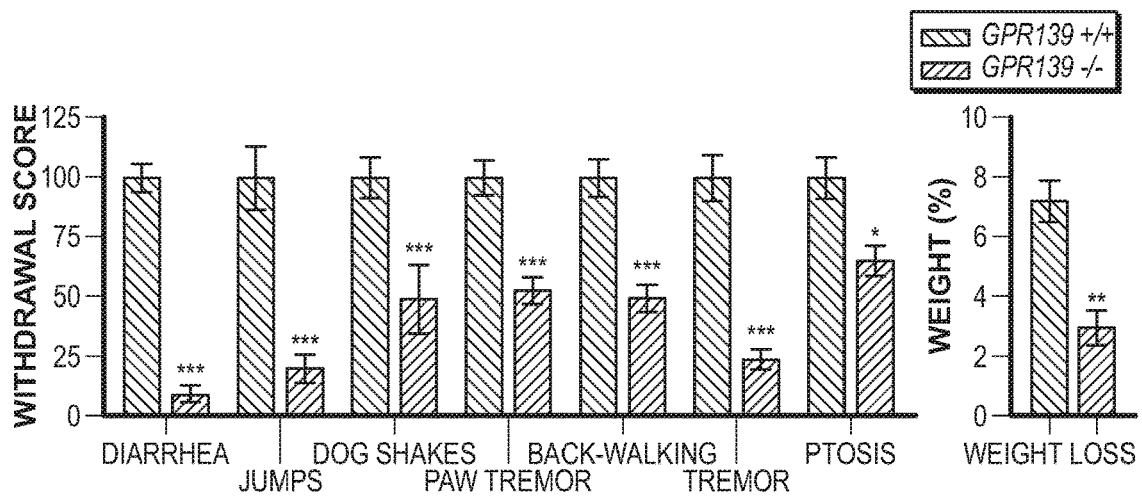
Figure 13A:
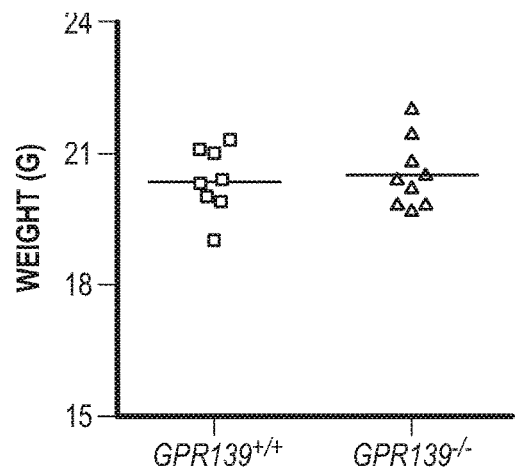
FIG. 13 shows that GPR139 knockout mice have normal weight, fat and muscle content. (A) Body weight of Gpr139$^{+/+}$ and Gpr139$^{-/-}$ mice at approximately 4 months old (n=8/9 per group); Student T-test unpaired two tailed p=0.7015. (B) Percent body fat of Gpr139$^{+/+}$ and Gpr139$^{-/-}$, mice at approximately 4 months old (n=8/9 per group): Student T-test unpaired two tailed p=0.8521. (C) Percent body muscle of Gpr139$^{+/+}$ and Gpr139$^{-/-}$ mice at approximately 4 months old (n=8/9 per group); Student t-test unpaired two tailedp=0.1223.
Figure 13B:
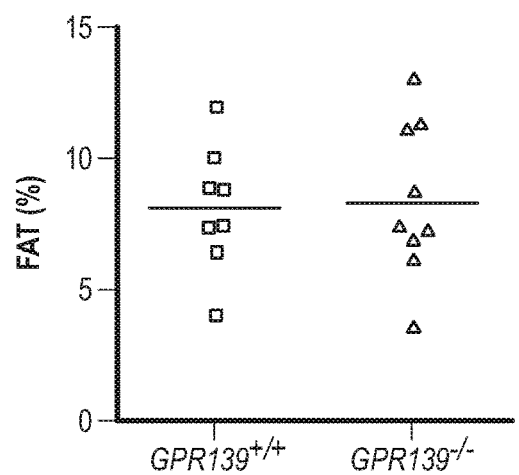
Figure 13C:
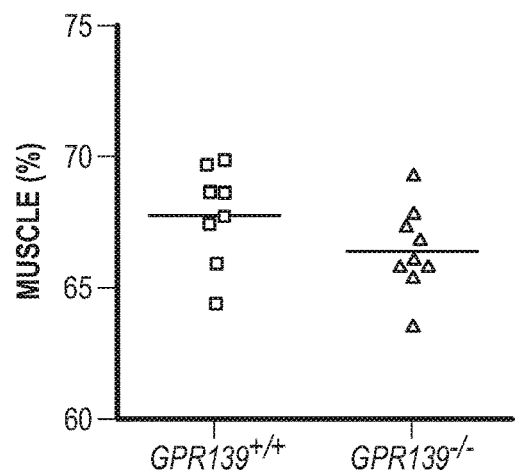
Figure 14A:
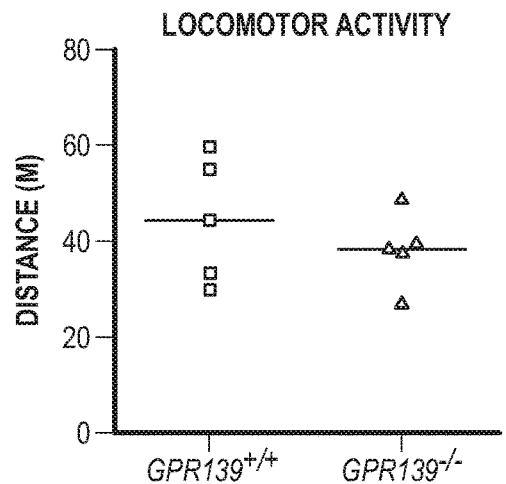
FIG. 14 shows that GRP139 knockouts have normal locomotion and motor learning. (A), Open Field (total distance; n=5 per group); p=0.3876. (B) Open Field distance over time (n=5 per group); Two way ANOVA interaction p=0.2404, time p<0.0001, genotype p=0.3876. (C) RotaRod (n=8/9 per group); Two way ANOVA interactionp>0.999, day p<0.0001, genotype p=0.5888.
Figure 14B:
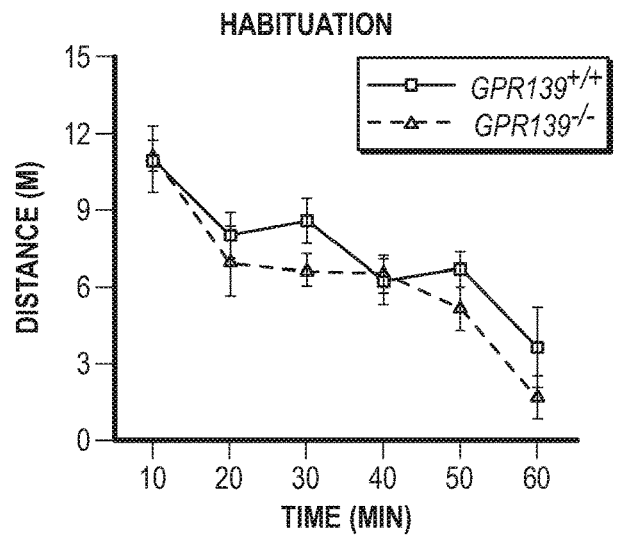
Figure 14C:
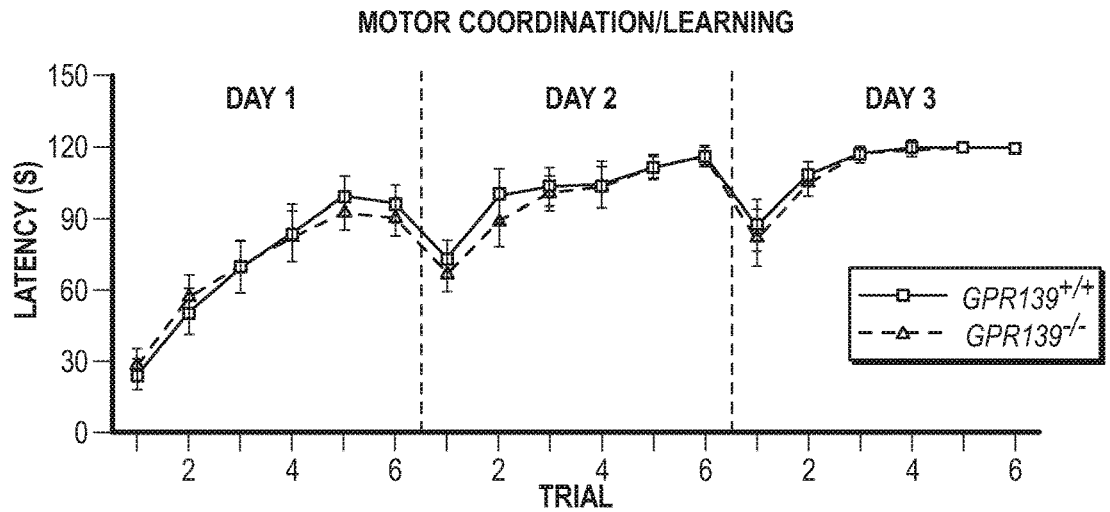

To probe the translational relevance of inhibitory influences of GPR139 on opioid signaling, we turned to in vivo mouse models. Consistent with previous studies (36, 37), we found that GPR139 is abundantly expressed in brain regions implicated in reward, analgesia and opioid action (FIG. 5A; FIG. S7). Importantly, GPR139 is extensively coexpressed with MOR in a number of neuronal populations in these areas including medial habenula, striatum, locus coeruleus, and periaqueductal grey matter (FIG. 5A; FIG. S7). To test how GPR139 impacts behavior, we obtained GPR139 knockout mice (Gpr139$^{-/-}$) where design of the targeted allele completely prevents the expression of GPR139 protein (FIG. 5B). Deletion of GPR139 had no overt effects on animal health and body composition (FIG. 13). Gpr139$^{-/-}$ mice were indistinguishable from their wild-type littermates in all baseline behaviors tested including baseline nociception (FIG. 5C), learning (FIG. 5E), locomotor activity, habituation to novel environment, and motor coordination (FIG. S9). Strikingly, the response of Gpr139$^{-/-}$ mice to morphine was markedly affected. When tested in a hot-plate assay, Gpr139$^{-/-}$ mice exhibited significantly increased morphine analgesia, including maximal response and duration of effect across multiple drug doses (FIG. 5C, D). Similarly, Gpr139$^{-/-}$ mice showed substantially augmented responses to the rewarding effects of morphine in a conditioned place preference paradigm (FIG. 5E). These results show that deletion of GPR139 increases sensitivity to the acute effects of morphine. Interestingly, we found that chronic morphine administration caused lower dependence in mice lacking GPR139, as revealed by diminished withdrawal across a spectrum of behaviors (FIG. 5F). Overall, these data indicate that GPR139 negatively regulates several behavioral responses to opioids.

Although the foregoing invention has been described in some detail by way of illustration and example for purposes of clarity of understanding, it will be readily apparent to one of ordinary skill in the art in light of the teachings of this invention that certain changes and modifications may be made thereto without departing from the spirit or scope of the appended claims.

All publications, databases, patents, and patent applications cited in this specification are herein incorporated by reference as if each was specifically and individually indicated to be incorporated by reference.

What is claimed is:

1. A method for providing or enhancing analgesic effect mediated by the μ-opioid receptor (MOR) in a subject, comprising administering to the subject a pharmaceutical composition comprising an effective amount of a compound that down-regulates expression or cellular activity of GPR139 or an ortholog thereof, wherein the compound is a small organic molecule, thereby enhancing MOR mediated analgesic effect in the subject.

2. The method of claim 1, wherein the subject is administered with an opioid drug for pain relief.

3. The method of claim 2, wherein the subject is administered with the opioid drug prior to, simultaneously with, or subsequent to administration of the pharmaceutical composition.

4. The method of claim 2, wherein the opioid drug is oxycodone, hydrocodone, morphine, codeine, fentanyl, buprenorphine or methadone.

5. The method of claim 1, wherein the subject is a human.

6. The method of claim 1, wherein the compound down-regulates GPCR signaling activity of GPR139 or an ortholog thereof.

7. The of claim 6, wherein the compound is selected from the following table:
| Compound Identifier | Compound Structure |
|---|---|
| NCRW0001-C02 | 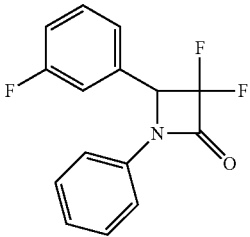 [SMILES: O=C1N(c2ccccc2)C(c2cccc(F)c2)C1(F)F] |
| NCRW0005-F05 | 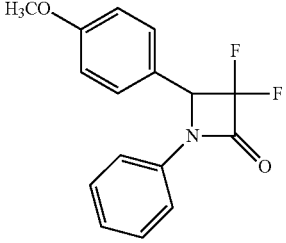 [SMILES: COc1ccc(C2N(c3ccccc3)C(=O)C2(F)F)cc1] |
| LP-114958 | 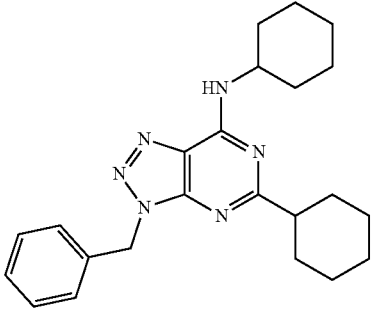 [SMILES: c1ccc(Cn2nnc3c(NC4CCCCC4)nc(C4CCCCC4)nc32)cc1] |
| LP-471756 | 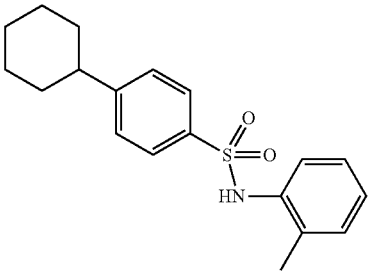 [SMILES: Cc1ccccc1NS(=O)(=O)c1ccc(C2CCCCC2)cc1] |
* * * * *

UNITED STATES PATENT AND TRADEMARK OFFICE
CERTIFICATE OF CORRECTION

| | | |
|---|---|---|
| PATENT NO. | : 12,042,496 B2 | Page 1 of 1 |
| APPLICATION NO. | : 17/286187 | |
| DATED | : July 23, 2024 | |
| INVENTOR(S) | : Kirill Martemyanov et al. | |

It is certified that error appears in the above-identified patent and that said Letters Patent is hereby corrected as shown below:

On the Title Page

At Item (71), Applicant, "University of FLorida Research Foundation, Incorporated" should read
-- University of Florida Research Foundation, Incorporated --.

Signed and Sealed this
Fifteenth Day of October, 2024

Katherine Kelly Vidal
*Director of the United States Patent and Trademark Office*